US011484294B2

(12) United States Patent
Hancock et al.

(10) Patent No.: US 11,484,294 B2
(45) Date of Patent: Nov. 1, 2022

(54) CLUTTER REDUCTION FOR ULTRASOUND IMAGES AND ASSOCIATED DEVICES, SYSTEMS, AND METHODS

(71) Applicant: KONINKLIJKE PHILIPS N.V., Eindhoven (NL)

(72) Inventors: Andrew Hancock, Sacramento, CA (US); Yiqun Yang, Sacramento, CA (US); David Hope Simpson, Bothell, WA (US); Francois Guy Gerard Marie Vignon, Andover, MA (US); Jun Seob Shin, Medford, MA (US)

(73) Assignee: PHILIPS IMAGE GUIDED THERAPY CORPORATION

( * ) Notice: Subject to any disclaimer, the term of this patent is extended or adjusted under 35 U.S.C. 154(b) by 43 days.

(21) Appl. No.: 16/750,223

(22) Filed: Jan. 23, 2020

(65) Prior Publication Data
US 2020/0245977 A1    Aug. 6, 2020

Related U.S. Application Data

(60) Provisional application No. 62/801,139, filed on Feb. 5, 2019.

(51) Int. Cl.
*A61B 8/12* (2006.01)
*A61B 8/14* (2006.01)
(Continued)

(52) U.S. Cl.
CPC .............. *A61B 8/5269* (2013.01); *A61B 8/12* (2013.01); *A61B 8/14* (2013.01); *A61B 8/445* (2013.01); *A61B 8/4488* (2013.01); *A61B 8/4494* (2013.01)

(58) Field of Classification Search
CPC ........... A61B 8/5269; A61B 8/12; A61B 8/14; A61B 8/445; A61B 8/4488; A61B 8/4494;
(Continued)

(56) References Cited

U.S. PATENT DOCUMENTS 6,776,763 B2    8/2004    Nix
7,226,417 B1 *   6/2007   Eberle .................. B06B 1/0633
                                                    29/25.35
(Continued)

FOREIGN PATENT DOCUMENTS

WO    2017011058 A1    1/2017
WO    2019057592 A1    3/2019

OTHER PUBLICATIONS

Selfridge et al "A Theory for the radiation Patter of a Narrow-Strip Acoustic Transducer", Applied Physics Letters, vol. 37(9a), Jul. 1980. Abstract Only.
(Continued)

*Primary Examiner* — Keith M Raymond
*Assistant Examiner* — Nicholas A Robinson

(57) ABSTRACT

Ultrasound imaging systems and methods for generated clutter-reduced images are provided. For example, an ultrasound imaging system can include an array of acoustic elements in communication with a processor. The processor is configured to activate the array to perform a scan sequence to obtain a plurality of signals, identify off-axis signals from the plurality of signals by comparing the right subaperture and the left subaperture, and create a clutter-reduced image based on the comparison. Because off-axis signals are more likely to create image clutter, reducing the influence of off-axis signals on the image can therefore improve the quality of the image. Accordingly, embodiments of the present disclosure provide systems, methods, and devices for generating ultrasound images that have reduced or
(Continued)

minimized clutter, even for images obtained using arrays that do not satisfy the Nyquist criterion.

19 Claims, 18 Drawing Sheets

(51) Int. Cl.
*A61B 8/08* (2006.01)
*A61B 8/00* (2006.01)

(58) Field of Classification Search
CPC ......... A61B 8/06; A61B 8/488; A61B 8/4461; G01S 7/52085; G01S 15/8927; G01S 15/892; G01S 7/52077
See application file for complete search history.

(56) References Cited

U.S. PATENT DOCUMENTS

| | | |
|---|---|---|
| 7,846,101 B2 | 12/2010 | Eberle |
| 8,254,654 B2 | 8/2012 | Yen |
| 2009/0141957 A1* | 6/2009 | Yen ..................... G01S 15/8977 600/437 |
| 2010/0168577 A1 | 7/2010 | Vezina |
| 2010/0234716 A1 | 9/2010 | Engel |
| 2015/0305710 A1 | 10/2015 | Stigall |
| 2019/0059851 A1 | 2/2019 | Rothberg |
| 2020/0008784 A1* | 1/2020 | Yamanaka ............... A61B 8/15 |

OTHER PUBLICATIONS

Seo, Chi Hyung et al "Sidelobe Suppression in Ultrasound Imaging using Dual Apodization with Cross-Correlation", IEEE Transacation on Ultrasonic Rerroelectric Frequency Control, vol. 55, No. 20, 2008. pp. 21998-2210.

Shin, Junseob et al Ultrasounic reverberation Clutter Suppression using Multiphase Apodization with Cross Correlation, IEEE Transactions on Ultrasonics, Ferroelectrics, and Frequency Control, vol. 53, No. 11, Nov. 2016, pp. 1947-1956.

Torbatian, Zahra et al "A Split-Aperture Transmit Beamforming technique with Phase Coherence Grating Lobe Suppression", IEEE Transactions on Ultrasonics, Ferroelectrics, and Frequency Control, vol. 57, No. 11, Nov. 2010, pp. 2588-2595.

* cited by examiner

FIG. 5

| | 18 | 19 | 20 | 21 | 22 | 23 | 24 | 25 | 26 | 27 | 28 | 29 | 30 | 31 | 32 | 33 | 34 |
|---|---|---|---|---|---|---|---|---|---|---|---|---|---|---|---|---|---|
| | | | 281 | 282 | 283 | 284 | 285 | 286 | 287 | 288 | 289 | 290 | 291 | 292 | 293 | 294 | |
| | | | 280 | 279 | 278 | 277 | 276 | 275 | 274 | 273 | 272 | 271 | 270 | 269 | 268 | 267 | |
| | | 253 | 254 | 255 | 256 | 257 | 258 | 259 | 260 | 261 | 262 | 263 | 264 | 265 | 266 | | |
| | 252 | 251 | 250 | 249 | 248 | 247 | 246 | 245 | 244 | 243 | 242 | 241 | 240 | 239 | | | |
| | 226 | 227 | 228 | 229 | 230 | 231 | 232 | 233 | 234 | 235 | 236 | 237 | 238 | | | | |
| | 222 | 221 | 220 | 219 | 218 | 217 | 216 | 215 | 214 | 213 | 212 | 211 | | | | | |
| | 200 | 201 | 202 | 203 | 204 | 205 | 206 | 207 | 208 | 209 | 210 | | | | | | |
| | 192 | 191 | 190 | 189 | 188 | 187 | 186 | 185 | 184 | 183 | | | | | | | |
| | 174 | 175 | 176 | 177 | 178 | 179 | 180 | 181 | 182 | | | | | | | | |
| | 162 | 161 | 160 | 159 | 158 | 157 | 156 | 155 | | | | | | | | | |
| | 148 | 149 | 150 | 151 | 152 | 153 | 154 | | | | | | | | | | |
| | 132 | 131 | 130 | 129 | 128 | 127 | | | | | | | | | | | |
| | 122 | 123 | 124 | 125 | 126 | | | | | | | | | | | | |
| | 102 | 101 | 100 | 99 | | | | | | | | | | | | | |
| | 96 | 97 | 98 | | | | | | | | | | | | | | |
| | 72 | 71 | | | | | | | | | | | | | | | |
| | 70 | | | | | | | | | | | | | | | | |

CLUTTER REDUCTION FOR ULTRASOUND IMAGES AND ASSOCIATED DEVICES, SYSTEMS, AND METHODS

CROSS-REFERENCE TO PRIOR APPLICATIONS

This application claims the benefit of U.S. Provisional Patent Application Ser. No. 62/801,139, filed Feb. 5, 2019 which is hereby incorporated by reference.

TECHNICAL FIELD

The present disclosure relates generally to ultrasound imaging and, in particular, to generating clutter-reduced ultrasound images. For example, an ultrasonic medical imaging device can include an array of acoustic elements configured to obtain ultrasound data, the array being in communication with a processor configured to process the obtained ultrasound data based on the directional receive characteristics of the array.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device including one or more ultrasound transducers is passed into the vessel and guided to the area to be imaged. The transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed.

Solid-state (also known as synthetic-aperture) IVUS catheters are one of the two types of IVUS devices commonly used today, the other type being the rotational IVUS catheter. Solid-state IVUS catheters carry a scanner assembly that includes an array of ultrasound transducers positioned and distributed around its perimeter or circumference along with one or more integrated circuit controller chips mounted adjacent to the transducer array. The controllers select individual acoustic elements (or groups of elements) for transmitting a pulse of acoustic energy and for receiving the ultrasound echo signal corresponding to the transmitted ultrasound energy. By stepping through a sequence of transmit-receive pairs, the solid-state IVUS system can synthesize the effect of a mechanically scanned ultrasound transducer but without moving parts (hence the solid-state designation). Since there is no rotating mechanical element, the transducer array can be placed in direct contact with the blood and vessel tissue with minimal risk of vessel trauma. Furthermore, because there is no rotating element, the electrical interface is simplified. The solid-state scanner can be wired directly to the imaging system with a simple electrical cable and a standard detachable electrical connector, rather than the complex rotating electrical interface required for a rotational IVUS device.

In IVUS imaging, a clinical goal is reducing ultrasound image artifacts, such as artifacts produced by grating lobes. Image clutter, which includes grating lobe and side lobe artifacts, is particularly common in ultrasound images that are spatially-undersampled. Spatially-undersampled images can result from arrays that do not satisfy the Nyquist sampling criterion, which requires that the pitch, or spacing between acoustic elements in the array, be smaller than half the center wavelength. Given the frequencies at which IVUS imaging devices operate, it may be difficult to manufacture IVUS imaging arrays with acoustic elements and spacings that are small enough to satisfy the Nyquist criterion.

SUMMARY

Aspects of the present disclosure generate ultrasound images with better image quality because they have fewer artifacts that result from clutter (e.g., grating lobes, side lobes). In particular, aspects of the present disclosure distinguish between on-axis signals and off-axis signals using different spatial groupings of transmit-receive pairs of a transducer array. Because on-axis signals are more likely to be representative of tissue, and off-axis signals are more likely to create image clutter, reducing the influence of off-axis signals on the image can therefore improve the quality of the image. Accordingly, embodiments of the present disclosure provide systems, methods, and devices for generating ultrasound images that have reduced or minimized clutter, even for images obtained using arrays that do not satisfy the Nyquist criterion. By grouping transmit-receive pairs of an array-based ultrasonic scan sequence into right and left subapertures, and comparing the right and left subapertures to distinguish on-axis signals from off-axis signals, weighting masks can be generated to reduce the influence or presence of artifacts and image clutter. In another aspect, the signals generated by the right and left subapertures can be used to generate image layers that represent different components of an ultrasound image, including tissue, noise, and lumen layers. An image having desirable components can be compiled using portions or aspects of each image layer.

In one embodiment, an ultrasound imaging system includes an array of acoustic elements configured to transmit acoustic energy into an anatomy and receive echoes corresponding to the transmitted acoustic energy, and a processor in communication with the array. The processor is configured to: activate the array to perform a scan sequence to obtain a plurality of signals, generate an image based on the plurality of signals, arrange the plurality of signals into a right subaperture and a left subaperture, identify off-axis signals from the plurality of signals by comparing the right subaperture and the left subaperture, generate a clutter reduction mask based on the identified off-axis signals, apply the clutter reduction mask to the image to generate a masked image, and output the masked image to a display in communication with the processor.

In some aspects, the scan sequence includes a plurality of transmit-receive pairs associated with the acoustic elements of the array, the plurality of signals corresponds to the plurality of transmit-receive pairs, and the processor is configured to: arrange signals associated with the right subaperture into a first right subaperture corresponding to a first portion of the transmit-receive pairs and a second right subaperture comprising a second portion of the transmit-receive pairs, wherein the first portion of the transmit-receive pairs and the second portion of the transmit-receive pairs are interleaving; and arrange transmit-receive pairs associated with the left subaperture into a first left subaperture comprising a third portion of the transmit-receive pairs and a second left subaperture comprising a fourth portion of the transmit-receive pairs, wherein the third portion of the transmit-receive pairs and the fourth portion of the transmit-receive pairs are interleaving. The processor is configured to identify the off-axis signals based on a relationship that includes the first and second right subapertures, and the first and second left subapertures.

In other aspects, the processor is configured to generate a noise image layer based on a relationship that includes the right and left subapertures, wherein the noise image layer comprises an image layer formed of isolated signals representative of noise in the image. In some embodiments, the processor is configured to generate the clutter reduction mask based in part on the noise image layer. In another aspect, the processor is configured to generate a tissue image layer based on a relationship that includes the right and left subapertures, the image, and the clutter reduction mask, wherein the tissue image layer comprises an image layer formed of isolated signals representative of tissue in the image. In another aspect, the processor is configured to generate a lumen image layer based on the tissue image layer and the clutter reduction mask, wherein the lumen image layer comprises an image layer formed of isolated signals representative of a body lumen in the image.

In some embodiments, the left subaperture and the right subaperture are part of an aperture, wherein the aperture comprises an axis. In one aspect, the left subaperture is spatially associated with a left side of the axis of the aperture and the right subaperture is spatially associated with a right side of the axis of the aperture. In some embodiments, the aperture is associated with an angular portion of a circumference of the array. In some embodiments, the off-axis signals are generated from ultrasound energy reflected from objects that are away from the axis of the aperture. In one aspect, the aperture is formed of a plurality of transmit-receive pairs of the scan sequence, wherein each of the plurality of transmit-receive pairs is associated with a transmit element of the aperture and a receive element of the aperture, wherein the right subaperture is formed of a first portion of the plurality of transmit-receive pairs representative of all of the transmit elements of the aperture and a portion of the receive elements of the aperture, and wherein the left subapertures is formed of a second portion of the plurality of transmit-receive pairs representative of a portion of the transmit elements of the aperture and all of the receive elements of the aperture. In some embodiments, the ultrasound imaging system further includes an intravascular ultrasound (IVUS) imaging catheter, and the array of acoustic elements is positioned around a perimeter of the IVUS imaging catheter.

In another aspect of the present disclosure, a method for ultrasound imaging includes activating an array of acoustic elements to perform a scan sequence to obtain a plurality of signals, generating, by a processor in communication with the array, an image based on the plurality of signals, arranging, by the processor, the plurality of signals into a right subaperture and a left subaperture, identifying, by the processor, off-axis signals from the plurality of signals by comparing the right subaperture and the left subaperture, generating, by the processor, a clutter reduction mask based on the identified off-axis signals, applying, by the processor, the clutter reduction mask to the image to generate a masked image, and outputting the masked image to a display in communication with the processor.

In some embodiments, activating the array to perform the scan sequence comprises activating a plurality of transmit-receive pairs associated with the acoustic elements of the array, wherein the plurality of signals corresponds to the plurality of transmit-receive pairs. The method can further include: arranging signals associated with the right subaperture into a first right subaperture corresponding to a first portion of the transmit-receive pairs and a second right subaperture comprising a second portion of the transmit-receive pairs, wherein the first portion of the transmit-receive pairs and the second portion of the transmit-receive pairs are interleaving; and arranging transmit-receive pairs associated with the left subaperture into a first left subaperture comprising a third portion of the transmit-receive pairs and a second left subaperture comprising a fourth portion of the transmit-receive pairs, wherein the third portion of the transmit-receive pairs and the fourth portion of the transmit-receive pairs are interleaving. Identifying the off-axis signals can include identifying the off-axis signals based on a relationship that includes the first and second right subapertures, and the first and second left subapertures.

In some aspects, the method includes generating a noise image layer based on a relationship that includes the right and left subapertures, wherein the noise image layer comprises an image layer formed of isolated signals representative of noise in the image. In another aspect, the method includes generating the clutter reduction mask based on the noise image layer. In still another aspect, the method includes generating a tissue image layer based on a relationship that includes the right and left subapertures, the image, and the clutter reduction mask, wherein the tissue image layer comprises an image layer formed of isolated signals representative of tissue in the image. In some embodiments, generating a lumen image layer based on the tissue image layer and the clutter reduction mask, wherein the lumen image layer comprises an image layer formed of isolated signals representative of a body lumen in the image.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 5 is a diagrammatic graphical view of an ultrasound pulse sequence, according to aspects of the present disclosure.

DETAILED DESCRIPTION

Figure 1:
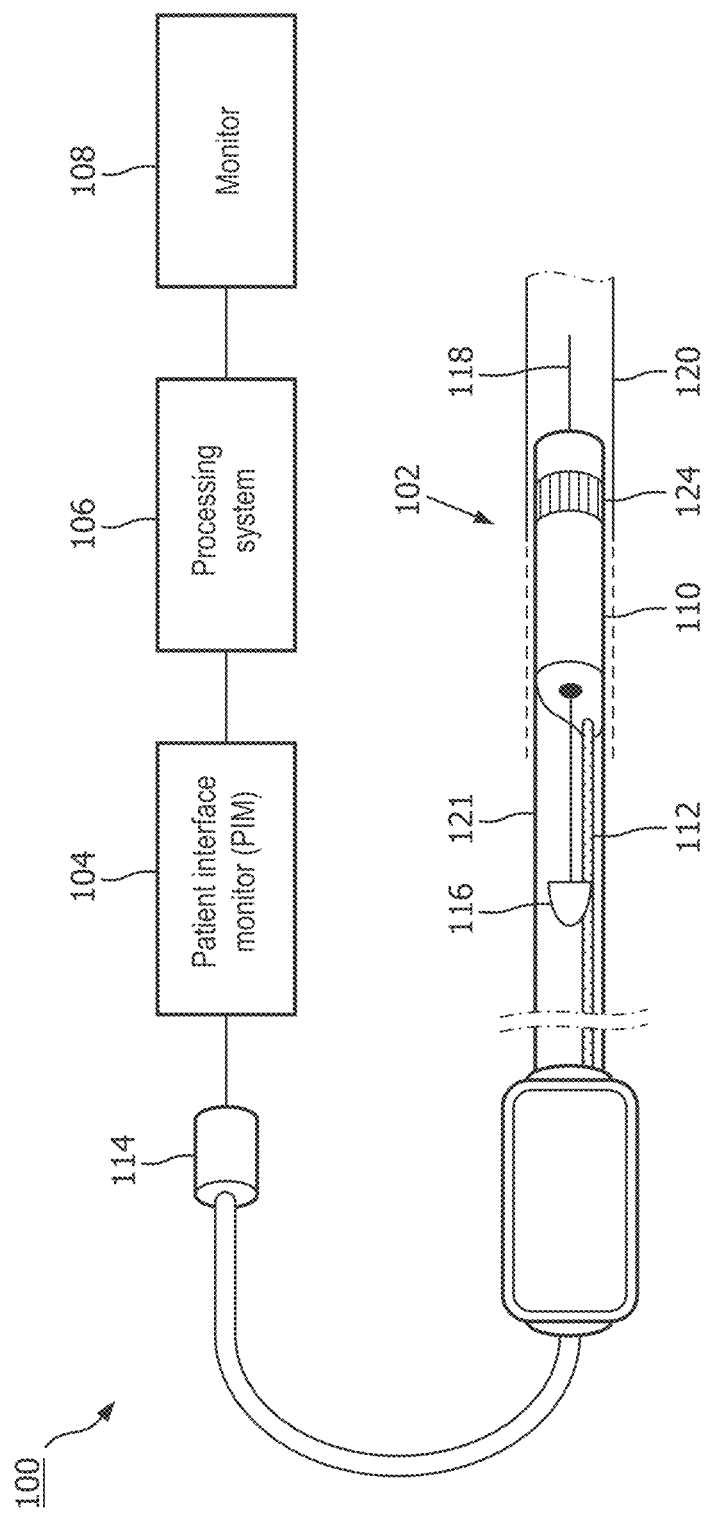
FIG. 1 is a diagrammatic schematic view of an intraluminal imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an ultrasound imaging system 100, according to aspects of the present disclosure. The ultrasound imaging system 100 can be an intraluminal imaging system. In some instances, the system 100 can be an intravascular ultrasound (IVUS) imaging system. The system 100 may include an intraluminal imaging device 102 such as a catheter, guide wire, or guide catheter, a patient interface module (PIM) 104, a processing system or console 106, and a monitor 108. The intraluminal imaging device 102 can be an ultrasound imaging device. In some instances, the device 102 can be IVUS imaging device, such as a solid-state IVUS device.

At a high level, the IVUS device 102 emits ultrasonic energy, or ultrasound signals, from a transducer array 124 included in scanner assembly 110 mounted near a distal end of the catheter device. The ultrasonic energy is reflected by tissue structures in the medium, such as a vessel 120, or another body lumen surrounding the scanner assembly 110, and the ultrasound echo signals are received by the transducer array 124. In that regard, the device 102 can be sized, shaped, or otherwise configured to be positioned within the body lumen of a patient. The PIM 104 transfers the received echo signals to the console or computer 106 where the ultrasound image (including the flow information) is reconstructed and displayed on the monitor 108. The console or computer 106 can include a processor and a memory. The computer or computing device 106 can be operable to facilitate the features of the IVUS imaging system 100 described herein. For example, the processor can execute computer readable instructions stored on the non-transitory tangible computer readable medium.

The PIM 104 facilitates communication of signals between the IVUS console 106 and the scanner assembly 110 included in the IVUS device 102. This communication includes the steps of: (1) providing commands to integrated circuit controller chip(s) 206A, 206B, illustrated in FIG. 2, included in the scanner assembly 110 to select the particular transducer array element(s), or acoustic element(s), to be used for transmit and receive, (2) providing the transmit trigger signals to the integrated circuit controller chip(s) 206A, 206B included in the scanner assembly 110 to activate the transmitter circuitry to generate an electrical pulse to excite the selected transducer array element(s), and/or (3) accepting amplified echo signals received from the selected transducer array element(s) via amplifiers included on the integrated circuit controller chip(s)126 of the scanner assembly 110. In some embodiments, the PIM 104 performs preliminary processing of the echo data prior to relaying the data to the console 106. In examples of such embodiments, the PIM 104 performs amplification, filtering, and/or aggregating of the data. In an embodiment, the PIM 104 also supplies high- and low-voltage DC power to support operation of the device 102 including circuitry within the scanner assembly 110.

The IVUS console 106 receives the echo data from the scanner assembly 110 by way of the PIM 104 and processes the data to reconstruct an image of the tissue structures in the medium surrounding the scanner assembly 110. The console 106 outputs image data such that an image of the vessel 120, such as a cross-sectional image of the vessel 120, is displayed on the monitor 108. Vessel 120 may represent fluid filled or surrounded structures, both natural and man-made. The vessel 120 may be within a body of a patient. The vessel 120 may be a blood vessel, as an artery or a vein of a patient's vascular system, including cardiac vasculature, peripheral vasculature, neural vasculature, renal vasculature, and/or or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be used to examine man-made structures such as, but without limitation, heart valves, stents, shunts, filters and other devices.

Figure 2:
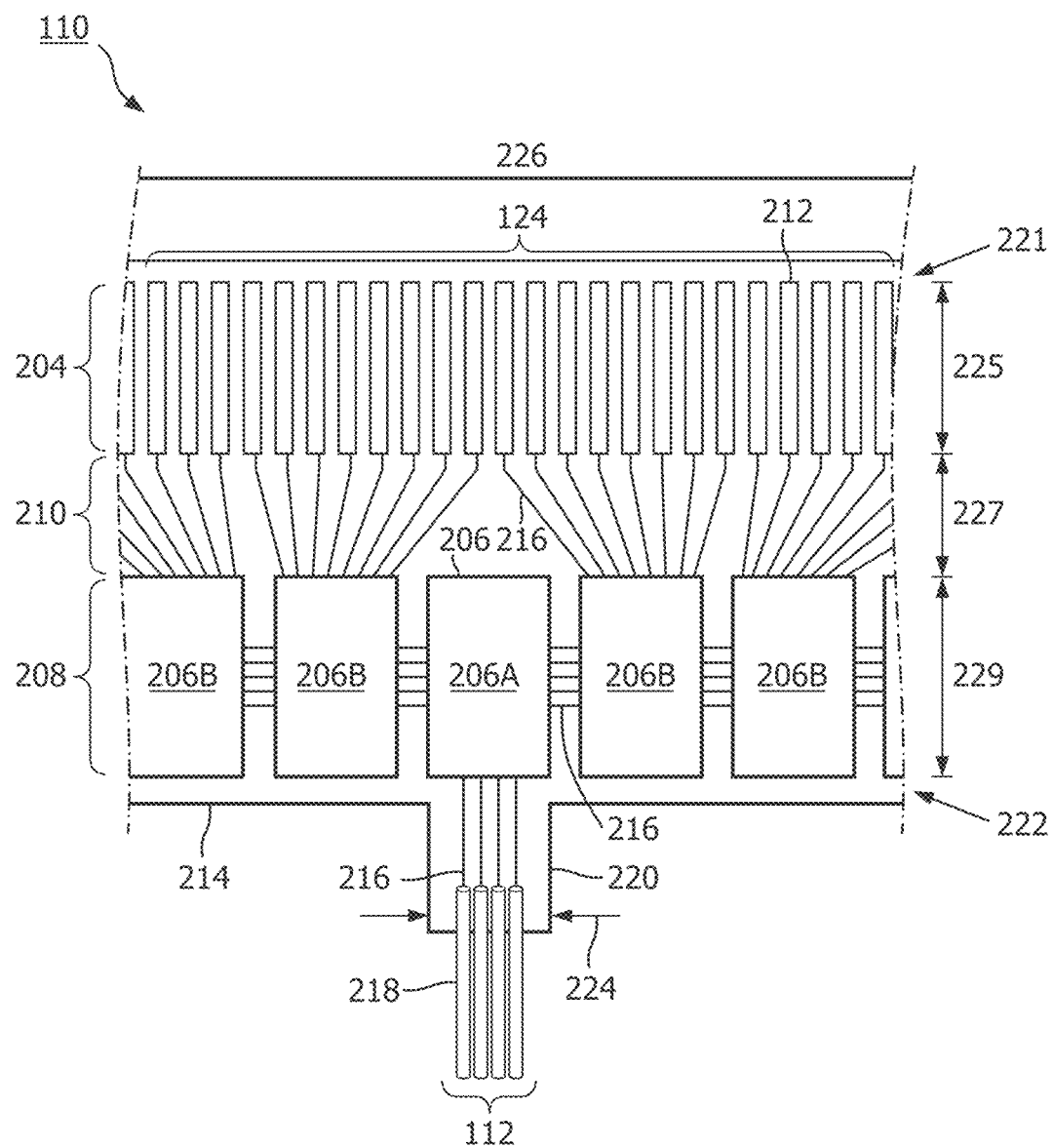
FIG. 2 is a diagrammatic view of the top of a scanner assembly in a flat configuration, according to aspects of the present disclosure.

In some embodiments, the IVUS device includes some features similar to traditional solid-state IVUS catheters, such as the EagleEye® catheter available from Koninklijke Philips N.V. and those disclosed in U.S. Pat. No. 7,846,101 hereby incorporated by reference in its entirety. For example, the IVUS device 102 includes the scanner assembly 110 near a distal end of the device 102 and a transmission line bundle 112 extending along the longitudinal body of the device 102. The transmission line bundle or cable 112 can include a plurality of conductors, including one, two, three, four, five, six, seven, or more conductors 218 (FIG. 2). It is understood that any suitable gauge wire can be used for the conductors 218. In an embodiment, the cable 112 can include a four-conductor transmission line arrangement with, e.g., 41 AWG gauge wires. In an embodiment, the cable 112 can include a seven-conductor transmission line arrangement utilizing, e.g., 44 AWG gauge wires. In some embodiments, 43 AWG gauge wires can be used.

The transmission line bundle 112 terminates in a PIM connector 114 at a proximal end of the device 102. The PIM connector 114 electrically couples the transmission line bundle 112 to the PIM 104 and physically couples the IVUS device 102 to the PIM 104. In an embodiment, the IVUS device 102 further includes a guide wire exit port 116. Accordingly, in some instances the IVUS device is a rapid-exchange catheter. The guide wire exit port 116 allows a guide wire 118 to be inserted towards the distal end in order to direct the device 102 through the vessel 120.

In an embodiment, the image processing system 106 generates flow data by processing the echo signals from the IVUS device 102 into Doppler power or velocity information. The image processing system 106 may also generate B-mode data by applying envelope detection and logarithmic compression on the conditioned echo signals. The processing system 106 can further generate images in various views, such as 2D and/or 3D views, based on the flow data or the B-mode data. The processing system 106 can also perform various analyses and/or assessments. For example, the processing system 106 can apply virtual histology (VH) techniques, for example, to analyze or assess plaques within a vessel (e.g., the vessel 120). The images can be generated to display a reconstructed color-coded tissue map of plaque composition superimposed on a cross-sectional view of the vessel.

In an embodiment, the processing system 106 can apply a blood flow detection algorithm (e.g., ChromaFlo) to determine the movement of blood flow, for example, by acquiring image data of a target region (e.g., the vessel 120) repeatedly and determining the movement of the blood flow from the image data. The blood flow detection algorithm operates based on the principle that signals measured from vascular tissue are relatively static from acquisition to acquisition, whereas signals measured from blood flow vary at a characteristic rate corresponding to the flow rate. As such, the blood flow detection algorithm may determine movements of blood flow based on variations in signals measured from the target region between repeated acquisitions. To acquire the image data repeatedly, the processing system 106 may control to the device 102 to transmit repeated pulses on the same aperture.

While the present disclosure describes embodiments related to intravascular ultrasound (IVUS) imaging using an intravascular catheter or guidewire, it is understood that one or more aspects of the present disclosure can be implemented in any suitable ultrasound imaging system, including a synthetic aperture ultrasound imaging system, a phased array ultrasound imaging system, or any other array-based ultrasound imaging system. For example, aspects of the present disclosure can be implemented in intraluminal ultrasound imaging systems using an intracardiac (ICE) echocardiography catheter and/or a transesophageal echocardiography (TEE) probe, and/or external ultrasound imaging system using an ultrasound probe configured for imaging while positioned adjacent to and/or in contact with the patient's skin. The ultrasound imaging device can be a transthoracic echocardiography (TTE) imaging device in some embodiments.

An ultrasound transducer array of ultrasound imaging device includes an array of acoustic elements configured to emit ultrasound energy and receive echoes corresponding to the emitted ultrasound energy. In some instances, the array may include any number of ultrasound transducer elements. For example, the array can include between 2 acoustic elements and 10000 acoustic elements, including values such as 2 acoustic elements, 4 acoustic elements, acoustic elements, 64 acoustic elements, 128 acoustic elements, 500 acoustic elements, 812 acoustic elements, 3000 acoustic elements, 9000 acoustic elements, and/or other values both larger and smaller. In some instances, the transducer elements of the array may be arranged in any suitable configuration, such as a linear array, a planar array, a curved array, a curvilinear array, a circumferential array, an annular array, a phased array, a matrix array, a one-dimensional (1D) array, a 1.x dimensional array (e.g., a 1.5D array), or a two-dimensional (2D) array. The array of transducer elements (e.g., one or more rows, one or more columns, and/or one or more orientations) can be uniformly or independently controlled and activated. The array can be configured to obtain one-dimensional, two-dimensional, and/or three-dimensional images of patient anatomy.

The ultrasound transducer elements may include piezoelectric/piezoresistive elements, piezoelectric micromachined ultrasound transducer (PMUT) elements, capacitive micromachined ultrasound transducer (CMUT) elements, and/or any other suitable type of ultrasound transducer elements. The ultrasound transducer elements of the array are in communication with (e.g., electrically coupled to) electronic circuitry. For example, the electronic circuitry can include one or more transducer control logic dies. The electronic circuitry can include one or more integrated circuits (IC), such as application specific integrated circuits (ASICs). In some embodiments, one or more of the ICs can include a microbeamformer (μBF). In other embodiments, one or more of the ICs includes a multiplexer circuit (MUX).

FIG. 2 is a diagrammatic top view of a portion of a flexible assembly 200, according to aspects of the present disclosure. The flexible assembly 200 includes a transducer array 124 formed in a transducer region 204 and transducer control logic dies 206 (including dies 206A and 206B) formed in a control region 208, with a transition region 210 disposed therebetween.

The transducer control logic dies 206 are mounted on a flexible substrate 214 into which the transducers 212 have been previously integrated. The flexible substrate 214 is shown in a flat configuration in FIG. 2. Though six control logic dies 206 are shown in FIG. 2, any number of control logic dies 206 may be used. For example, one, two, three, four, five, six, seven, eight, nine, ten, or more control logic dies 206 may be used.

The flexible substrate 214, on which the transducer control logic dies 206 and the transducers 212 are mounted, provides structural support and interconnects for electrical coupling. The flexible substrate 214 may be constructed to include a film layer of a flexible polyimide material such as KAPTON™ (trademark of DuPont). Other suitable materials include polyester films, polyimide films, polyethylene napthalate films, or polyetherimide films, liquid crystal polymer, other flexible printed semiconductor substrates as well as products such as Upilex® (registered trademark of Ube Industries) and TEFLON® (registered trademark of E.I. du Pont). In the flat configuration illustrated in FIG. 2, the flexible substrate 214 has a generally rectangular shape. As shown and described herein, the flexible substrate 214 is configured to be wrapped around a support member 230 (FIG. 3) in some instances. Therefore, the thickness of the film layer of the flexible substrate 214 is generally related to the degree of curvature in the final assembled flexible assembly 110. In some embodiments, the film layer is between 5 µm and 100 µm, with some particular embodiments being between 5 µm and 25.1 µm, e.g., 6 µm.

The transducer control logic dies 206 is a non-limiting example of a control circuit. The transducer region 204 is disposed at a distal portion 221 of the flexible substrate 214. The control region 208 is disposed at a proximal portion 222 of the flexible substrate 214. The transition region 210 is disposed between the control region 208 and the transducer region 204. Dimensions of the transducer region 204, the control region 208, and the transition region 210 (e.g., lengths 225, 227, 229) can vary in different embodiments. In some embodiments, the lengths 225, 227, 229 can be substantially similar or, the length 227 of the transition region 210 may be less than lengths 225 and 229, the length 227 of the transition region 210 can be greater than lengths 225, 229 of the transducer region and controller region, respectively.

The control logic dies 206 are not necessarily homogenous. In some embodiments, a single controller is designated a master control logic die 206A and contains the communication interface for cable 142 which may serve as an electrical conductor, e.g., electrical conductor 112, between a processing system, e.g., processing system 106, and the flexible assembly 200. Accordingly, the master control circuit may include control logic that decodes control signals received over the cable 142, transmits control responses over the cable 142, amplifies echo signals, and/or transmits the echo signals over the cable 142. The remaining controllers are slave controllers 206B. The slave controllers 206B may include control logic that drives a transducer 212 to emit an ultrasonic signal and selects a transducer 212 to receive an echo. In the depicted embodiment, the master controller 206A does not directly control any transducers 212. In other embodiments, the master controller 206A drives the same number of transducers 212 as the slave controllers 206B or drives a reduced set of transducers 212 as compared to the slave controllers 206B. In an exemplary embodiment, a single master controller 206A and eight slave controllers 206B are provided with eight transducers assigned to each slave controller 206B.

To electrically interconnect the control logic dies 206 and the transducers 212, in an embodiment, the flexible substrate 214 includes conductive traces 216 formed in the film layer that carry signals between the control logic dies 206 and the transducers 212. In particular, the conductive traces 216 providing communication between the control logic dies 206 and the transducers 212 extend along the flexible substrate 214 within the transition region 210. In some instances, the conductive traces 216 can also facilitate electrical communication between the master controller 206A and the slave controllers 206B. The conductive traces 216 can also provide a set of conductive pads that contact the conductors 218 of cable 142 when the conductors 218 of the cable 142 are mechanically and electrically coupled to the flexible substrate 214. Suitable materials for the conductive traces 216 include copper, gold, aluminum, silver, tantalum, nickel, and tin, and may be deposited on the flexible substrate 214 by processes such as sputtering, plating, and etching. In an embodiment, the flexible substrate 214 includes a chromium adhesion layer. The width and thickness of the conductive traces 216 are selected to provide proper conductivity and resilience when the flexible substrate 214 is rolled. In that regard, an exemplary range for the thickness of a conductive trace 216 and/or conductive pad is between 1-5 µm. For example, in an embodiment, 5 µm conductive traces 216 are separated by 5 µm of space. The width of a conductive trace 216 on the flexible substrate may be further determined by the width of the conductor 218 to be coupled to the trace/pad.

The flexible substrate 214 can include a conductor interface 220 in some embodiments. The conductor interface 220 can be a location of the flexible substrate 214 where the conductors 218 of the cable 142 are coupled to the flexible substrate 214. For example, the bare conductors of the cable 142 are electrically coupled to the flexible substrate 214 at the conductor interface 220. The conductor interface 220 can be tab extending from the main body of flexible substrate 214. In that regard, the main body of the flexible substrate 214 can refer collectively to the transducer region 204, controller region 208, and the transition region 210. In the illustrated embodiment, the conductor interface 220 extends from the proximal portion 222 of the flexible substrate 214. In other embodiments, the conductor interface 220 is positioned at other parts of the flexible substrate 214, such as the distal portion 221, or the flexible substrate 214 may lack the conductor interface 220. A value of a dimension of the tab or conductor interface 220, such as a width 224, can be less than the value of a dimension of the main body of the flexible substrate 214, such as a width 226. In some embodiments, the substrate forming the conductor interface 220 is made of the same material(s) and/or is similarly flexible as the flexible substrate 214. In other embodiments, the conductor interface 220 is made of different materials and/or is comparatively more rigid than the flexible substrate 214. For example, the conductor interface 220 can be made of a plastic, thermoplastic, polymer, hard polymer, etc., including polyoxymethylene (e.g., DELRIN®), polyether ether ketone (PEEK), nylon, Liquid Crystal Polymer (LCP), and/or other suitable materials.

Figure 3:
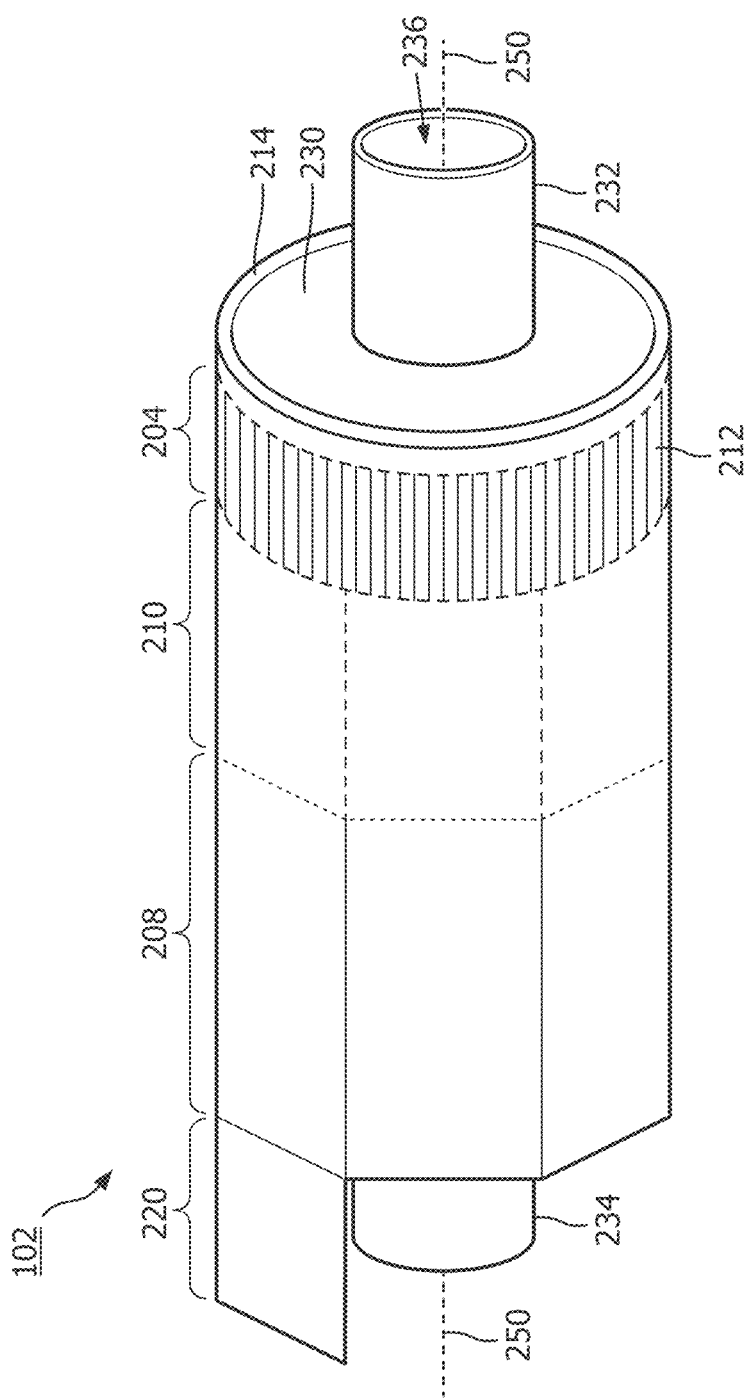
FIG. 3 is a diagrammatic perspective view of the scanner assembly shown in FIG. 2 in a rolled configuration around a support member, according to aspects of the present disclosure.

FIG. 3 illustrates a perspective view of the device 102 with the scanner assembly 110 in a rolled configuration. In some instances, the assembly 110 is transitioned from a flat configuration (FIG. 2) to a rolled or more cylindrical configuration (FIG. 3). For example, in some embodiments, techniques are utilized as disclosed in one or more of U.S. Pat. No. 6,776,763, titled "ULTRASONIC TRANSDUCER ARRAY AND METHOD OF MANUFACTURING THE SAME" and U.S. Pat. No. 7,226,417, titled "HIGH RESOLUTION INTRAVASCULAR ULTRASOUND SENSING ASSEMBLY HAVING A FLEXIBLE SUBSTRATE," each of which is hereby incorporated by reference in its entirety.

In some embodiments, the transducer elements 212 and/or the controllers 206 can be positioned in in an annular configuration, such as a circular configuration or in a polygon configuration, around a longitudinal axis 250 of a support member 230. It will be understood that the longitudinal axis 250 of the support member 230 may also be referred to as the longitudinal axis of the scanner assembly 110, the flexible elongate member 121, and/or the device 102. For example, a cross-sectional profile of the imaging assembly 110 at the transducer elements 212 and/or the controllers 206 can be a circle or a polygon. Any suitable annular polygon shape can be implemented, such as a based on the number of controllers/transducers, flexibility of the controllers/transducers, etc., including a pentagon, hexagon, heptagon, octagon, nonagon, decagon, etc. In some examples, the plurality of transducer controllers 206 may be used for controlling the plurality of ultrasound transducer elements 212 to obtain imaging data associated with the vessel 120.

The support member 230 can be referenced as a unibody in some instances. The support member 230 can be composed of a metallic material, such as stainless steel, or non-metallic material, such as a plastic or polymer as described in U.S. Provisional Application No. 61/985,220, "Pre-Doped Solid Substrate for Intravascular Devices," filed Apr. 28, 2014, ('220 Application) the entirety of which is hereby incorporated by reference herein. The support member 230 can be a ferrule having a distal flange or portion 232 and a proximal flange or portion 234. The support member 230 can be tubular in shape and define a lumen 236 extending longitudinally therethrough. The lumen 236 can be sized and shaped to receive the guide wire 118. The support member 230 can be manufactured using any suitable process. For example, the support member 230 can be machined and/or electrochemically machined or laser milled, such as by removing material from a blank to shape the support member 230, or molded, such as by an injection molding process.

Figure 4:
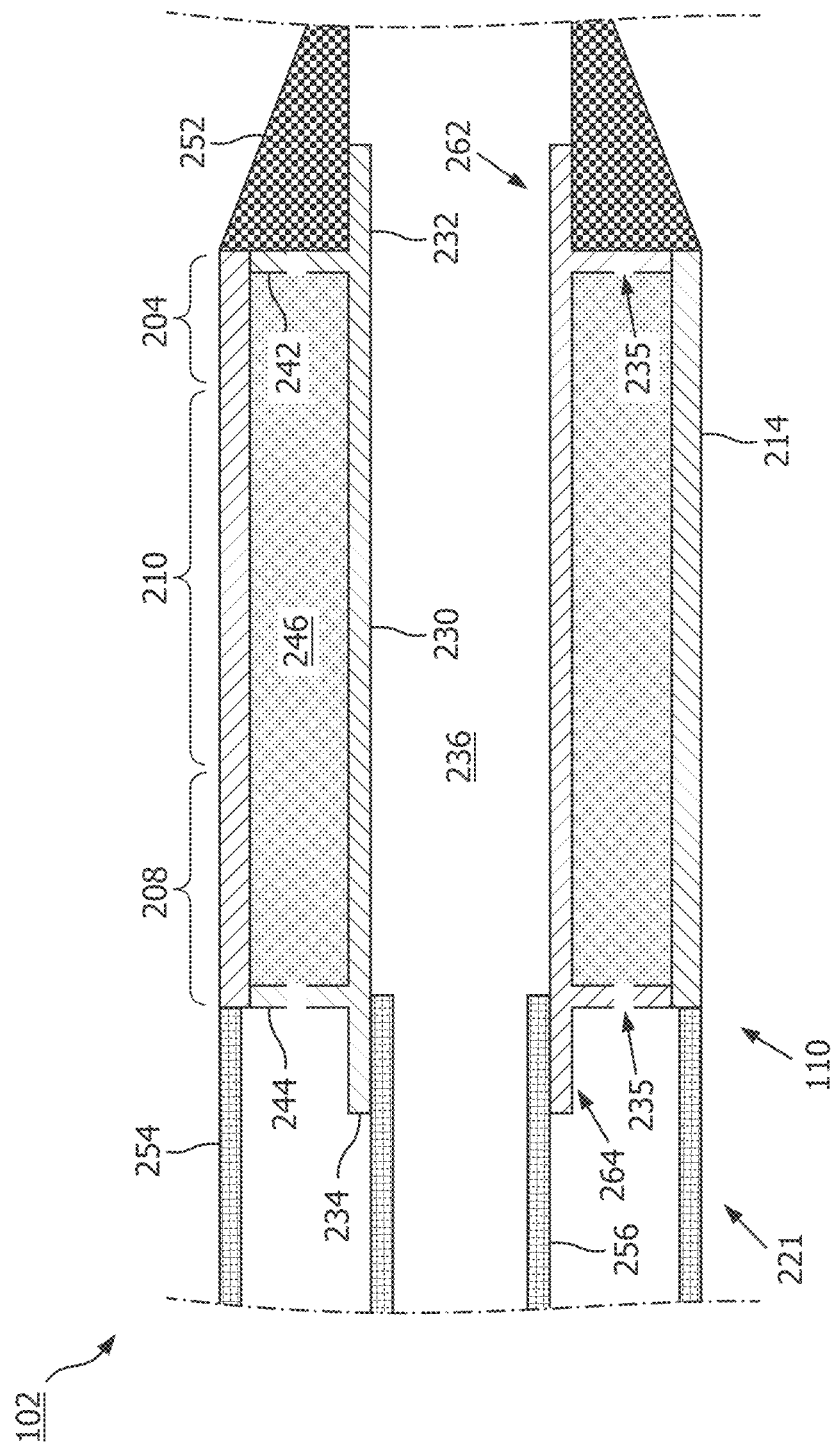
FIG. 4 is a diagrammatic cross-sectional side view of a scanner assembly in a rolled configuration around a support member, according to aspects of the present disclosure.

Referring now to FIG. 4, shown there is a diagrammatic cross-sectional side view of a distal portion of the intraluminal imaging device 102, including the flexible substrate 214 and the support member 230, according to aspects of the present disclosure. The support member 230 can be referenced as a unibody in some instances. The support member 230 can be composed of a metallic material, such as stainless steel, or non-metallic material, such as a plastic or polymer as described in U.S. Provisional Application No. 61/985,220, "Pre-Doped Solid Substrate for Intravascular Devices," filed Apr. 28, 2014, the entirety of which is hereby incorporated by reference herein. The support member 230 can be ferrule having a distal portion 262 and a proximal portion 264. The support member 230 can define a lumen 236 extending along the longitudinal axis LA. The lumen 236 is in communication with the entry/exit port 116 and is sized and shaped to receive the guide wire 118 (FIG. 1). The support member 230 can be manufactured according to any suitable process. For example, the support member 230 can be machined and/or electrochemically machined or laser milled, such as by removing material from a blank to shape the support member 230, or molded, such as by an injection molding process. In some embodiments, the support member 230 may be integrally formed as a unitary structure, while in other embodiments the support member 230 may be formed of different components, such as a ferrule and stands 242, 244, that are fixedly coupled to one another. In some cases, the support member 230 and/or one or more components thereof may be completely integrated with inner member 256. In some cases, the inner member 256 and the support member 230 may be joined as one, e.g., in the case of a polymer support member.

Stands 242, 244 that extend vertically are provided at the distal and proximal portions 262, 264, respectively, of the support member 230. The stands 242, 244 elevate and support the distal and proximal portions of the flexible substrate 214. In that regard, portions of the flexible substrate 214, such as the transducer portion or region 204, can be spaced from a central body portion of the support member 230 extending between the stands 242, 244. The stands 242, 244 can have the same outer diameter or different outer diameters. For example, the distal stand 242 can have a larger or smaller outer diameter than the proximal stand 244 and can also have special features for rotational alignment as well as control chip placement and connection. To improve acoustic performance, any cavities between the flexible substrate 214 and the surface of the support member 230 are filled with a backing material 246. The liquid backing material 246 can be introduced between the flexible substrate 214 and the support member 230 via passageways 235 in the stands 242, 244. In some embodiments, suction can be applied via the passageways 235 of one of the stands 242, 244, while the liquid backing material 246 is fed between the flexible substrate 214 and the support member 230 via the passageways 235 of the other of the stands 242, 244. The backing material can be cured to allow it to solidify and set. In various embodiments, the support member 230 includes more than two stands 242, 244, only one of the stands 242, 244, or neither of the stands. In that regard the support member 230 can have an increased diameter distal portion 262 and/or increased diameter proximal portion 264 that is sized and shaped to elevate and support the distal and/or proximal portions of the flexible substrate 214.

The support member 230 can be substantially cylindrical in some embodiments. Other shapes of the support member 230 are also contemplated including geometrical, non-geometrical, symmetrical, non-symmetrical, cross-sectional profiles. As the term is used herein, the shape of the support member 230 may reference a cross-sectional profile of the support member 230. Different portions the support member 230 can be variously shaped in other embodiments. For example, the proximal portion 264 can have a larger outer diameter than the outer diameters of the distal portion 262 or a central portion extending between the distal and proximal portions 262, 264. In some embodiments, an inner diameter of the support member 230 (e.g., the diameter of the lumen 236) can correspondingly increase or decrease as the outer diameter changes. In other embodiments, the inner diameter of the support member 230 remains the same despite variations in the outer diameter.

A proximal inner member 256 and a proximal outer member 254 are coupled to the proximal portion 264 of the support member 230. The proximal inner member 256 and/or the proximal outer member 254 can include a flexible elongate member. The proximal inner member 256 can be received within a proximal flange 234. The proximal outer member 254 abuts and is in contact with the flexible substrate 214. A distal member 252 is coupled to the distal portion 262 of the support member 230. For example, the distal member 252 is positioned around the distal flange 232. The distal member 252 can abut and be in contact with the flexible substrate 214 and the stand 242. The distal member 252 can be the distal-most component of the intraluminal imaging device 102.

One or more adhesives can be disposed between various components at the distal portion of the intraluminal imaging device 102. For example, one or more of the flexible substrate 214, the support member 230, the distal member 252, the proximal inner member 256, and/or the proximal outer member 254 can be coupled to one another via an adhesive.

Figure 5:
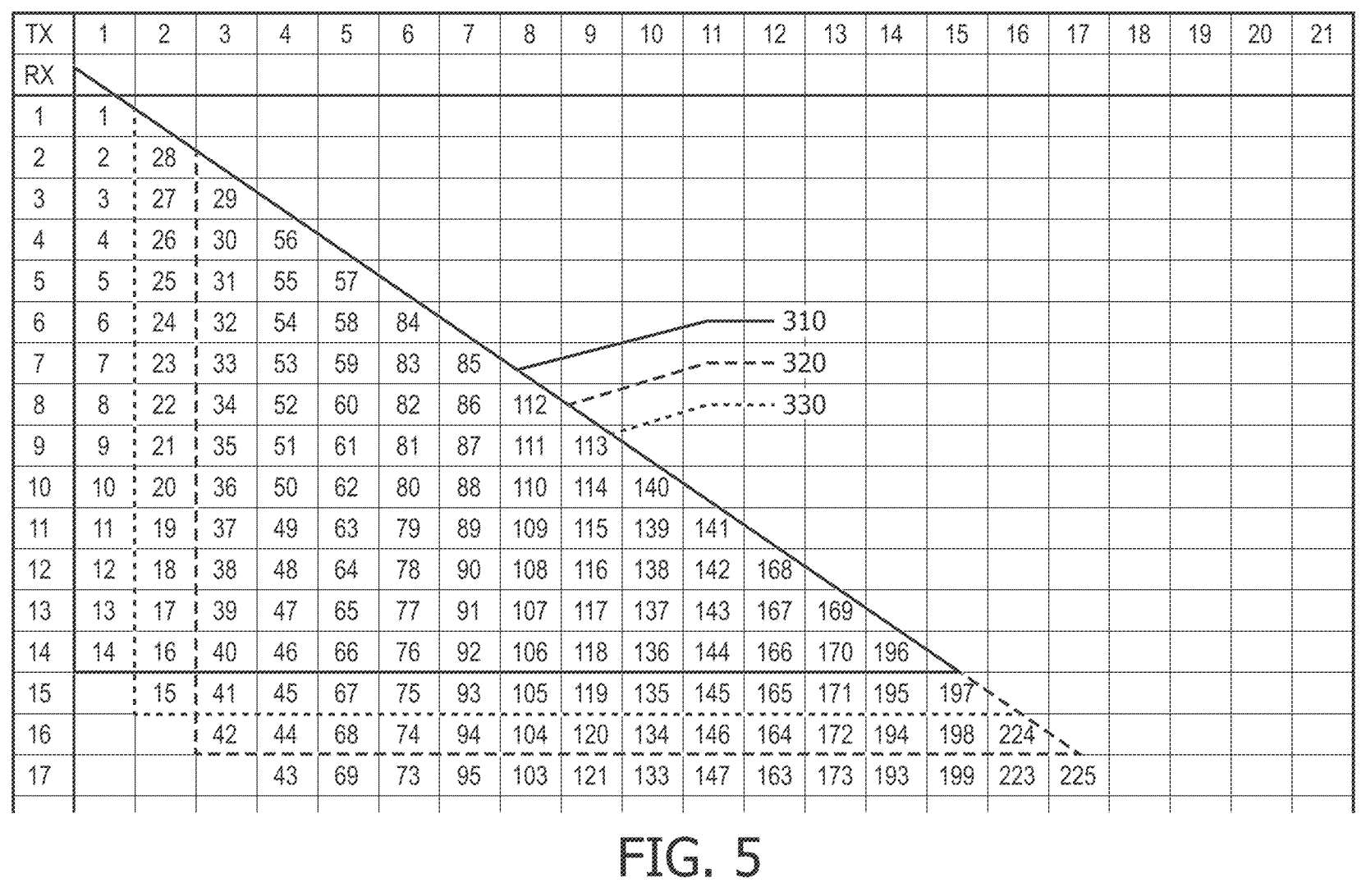

The assembly 110 shown in FIG. 2 can be activated according to a pulse sequence or scan sequence to form coherent beams of ultrasound energy to generate an image. In that regard, FIG. 5 is a diagrammatic graphical view showing an ultrasound pulse sequence of a solid-state IVUS device. The pulse sequence 300 includes a contiguous "zig-zag" pattern or arrangement of transmit-receive pairs, which can alternatively be described as transmit-receive events. Each transmit-receive pair is represented by an index, or number, corresponding to a sequential time at which the corresponding transmit-receive pair is activated to obtain ultrasound imaging data. In that regard, each transmit-receive index is an integer representing its relative temporal position in the sequence 300. In the embodiment of FIG. 5, each transmit-receive index corresponds to a single transmit-receive pair. Each transmit-receive pair is defined by a transmit element index, shown on the x-axis, and a receive element index, shown on the y-axis. Each transmit element index and receive element index corresponds to an ultrasound element of an array of ultrasound transducer elements. In the embodiment shown in FIG. 5, the array includes 64 ultrasound transducer elements. It may be advantageous in some circumstances, for instance to improve sensitivity or limit element directivity, to transmit or receive on more than one element at a time following a similar arrangement to that described above and illustrated in FIG. 5. The term "transmit element" as used here and throughout this document may therefore be taken to represent one or more physical elements transmitting together and associated with a nominal transmit element location within the array. Similarly, the term "receive element" as used here and throughout this document, may therefore be taken to represent one or more physical elements connected together with a nominal receive element location within the array.

For example, the transmit-receive pair associated with transmit-receive index "1" is defined by transmit element index number 1 and receive element index 1. In some embodiments, the transmit element index and receive element index correspond to the same ultrasound transducer element. In other embodiments, the transmit element index and receive element index correspond to different ultrasound transducer elements. For example, the transmit-receive pair numbered "2," which is shown directly below transmit-receive pair 1, is defined by transmit element index 1 and receive element index 2. That is, the ultrasound imaging data associated with transmit-receive pair 2 is obtained by activating transmit element index 1 to transmit ultrasound energy into the patient volume, and then activating receive element index 2 to receive ultrasound echoes from the patient volume. In FIG. 5, 294 transmit-receive pairs of an ultrasound pulse sequence are shown. Each transmit-receive pair is activated sequentially according to its transmit-receive index.

In the sequence 300, the ultrasound transducer element associated with transmit index 1 transmits fourteen consecutive times, while the elements associated with receive indices 1 through 14 are sequentially activated to receive the corresponding echoes. Next, the element associated with transmit index 2 transmits fourteen consecutive times, while the elements associated with receive indices 15 through 2 (stepping backward) are sequentially activated to receive the corresponding echoes. This sequence continues in a zig-zag pattern around the array of ultrasound transducer elements. Each transmit-receive pair is associated with one or more apertures 310, 320, 330. The apertures 310, 320, 330 are associated with different sections, angular portions, or arcs of the array. For example, a first aperture 310 includes transmit-receive pairs spanning from index 1 to index 196, a second aperture 320 includes transmit-receive pairs spanning from index 15 to index 197, and a third aperture 330 includes transmit-receive pairs spanning from index 29 to index 224. The transmit-receive pairs in each aperture are combined to form an A-line for a B-mode image. Thus, the transmit-receive pairs contained within the first aperture 310 are combined to form a first A-line, the transmit-receive pairs contained within the second aperture 320 are combined to form a second A-line, the transmit-receive pairs contained within the third aperture are combined to form a third A-line, and so on. The A-line formed by the first aperture 310 will be centered between transmit and receive element indices 7 and 8, the A-line formed by the second aperture 320 will be centered between transmit and receive element indices numbered 8 and 9, the A-line formed by the third aperture 330 will be centered between transmit and receive element indices numbered 9 and 10, and so on. Several apertures are used to form A-lines, which are combined and arranged to form a B-mode image.

It will be understood that the scan sequence shown in FIG. 5 is exemplary and that other scanning sequences can be used besides that sequence shown in FIG. 5. For example, the present disclosure contemplates scan sequences using patterns of transmit-receive pairs, aperture sizes, and combinations of transmit and receive pairs that are different from those described above.

Figure 6A:
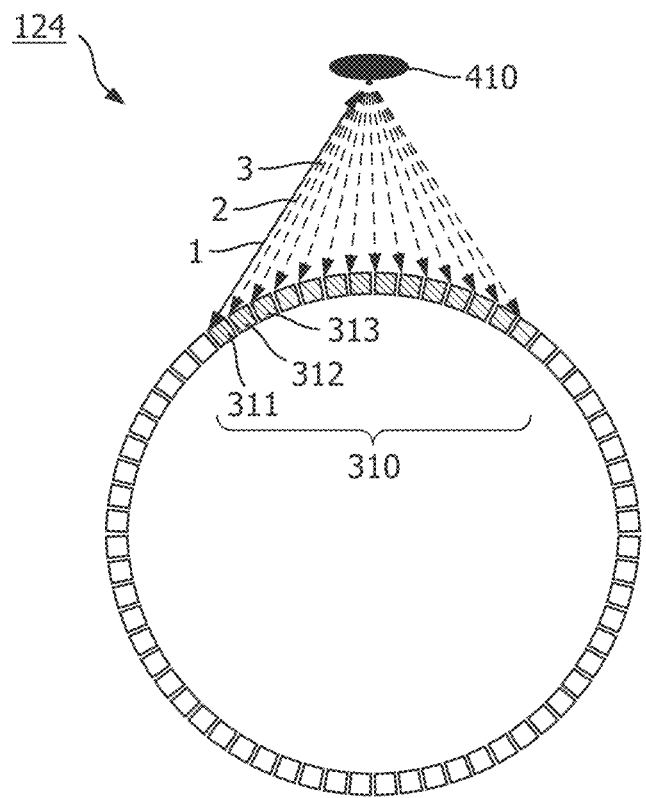
FIGS. 6A and 6B are diagrammatic schematic views of an array of acoustic elements with an aperture activated to obtain image data of a target, according to aspects of the present disclosure.
Figure 6B:
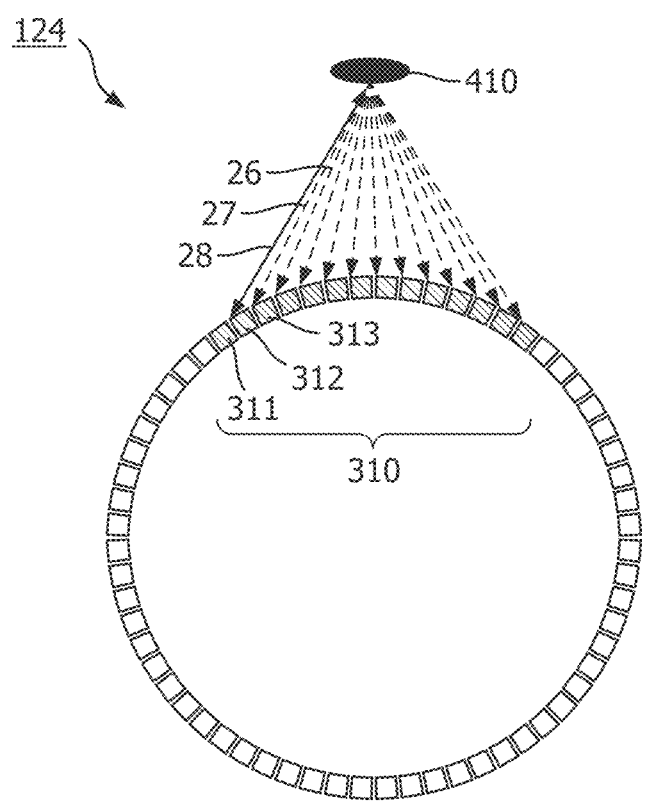

FIGS. 6A and 6B depict an annular array of an IVUS imaging device performing a portion of the scan sequence 300 shown in FIG. 5. In particular, FIGS. 6A and 6B show a portion of the scan sequence 300 associated with the first aperture 310. The first aperture 310 spans fourteen elements of the array 124. In the scan sequence 300, the first aperture 310 includes a plurality of transmit-receive pairs or firings, which are characterized by a transmit element index and a receive element index. In FIG. 6A, a first element 311 is the transmitting element, and each of the elements of the aperture 310, including the first element 311, sequentially receive ultrasound energy transmitted by the first element 311 and reflected off an object 410. In that regard, transmit-receive pair 1 is illustrated by the bold arrow in which the first element 311 is both the transmitting element and the receiving element. Transmit-receive pair 2 is characterized by ultrasound energy transmitted by the first element 311 and received by a second element 312. Transmit-receive pair 3 is characterized by ultrasound energy transmitted by the first element 311 and received by a third element 313. This transmit-receive sequence is repeated so that all fourteen elements of the aperture 310 have received ultrasound energy transmitted by the first element 311.

In FIG. 6B, the scan sequence continues with the second element 312 transmitting, and each of the remaining elements sequentially receiving the ultrasound energy transmitted by the second element 312, as similarly described above. It will be understood that, as shown in FIG. 6B, the first element 311 does not receive ultrasound energy transmitted by the second element 312. As explained further below, the first element 311 may not receive ultrasound energy transmitted by the second element 312 due to the signal reciprocity rule.

Ideally, ultrasound energy received by the elements of the array come from objects that are positioned on-axis with respect to the active aperture, such as the object 410. However, ultrasound energy transmitted by the elements may propagate in a wide range of transmission angles, and each of the elements may receive reflected ultrasound energy from a wide range of acceptance angles. The range of acceptance angles at which an element can receive reflected ultrasound energy can be described by its directivity, which is further described below with respect to FIGS. 7A and 7B.

Based on the directivity of the elements of the array 124, apertures of the array 124 may receive some signals from off-axis objects. Signals received from off-axis objects can result in image clutter, such as side lobe and grating lobe artifacts. Side lobe and grating lobe artifacts can appear in an image due to the off-axis object reflecting an unfocused portion (e.g., a grating lobe) of an ultrasound pulse back to the acoustic elements of the array. Ultrasound transducer arrays that do not satisfy the Nyquist criteria may be particularly likely to produce images that include grating lobe artifacts. These artifacts can appear in B-mode ultrasound images as blurry duplicates of the off-axis target, adding unwanted image clutter that complicates the image analysis process and makes it difficult for the physician or ultrasound technician to interpret ultrasound images, such as the tissue structure of a blood vessel.

Figure 7A:
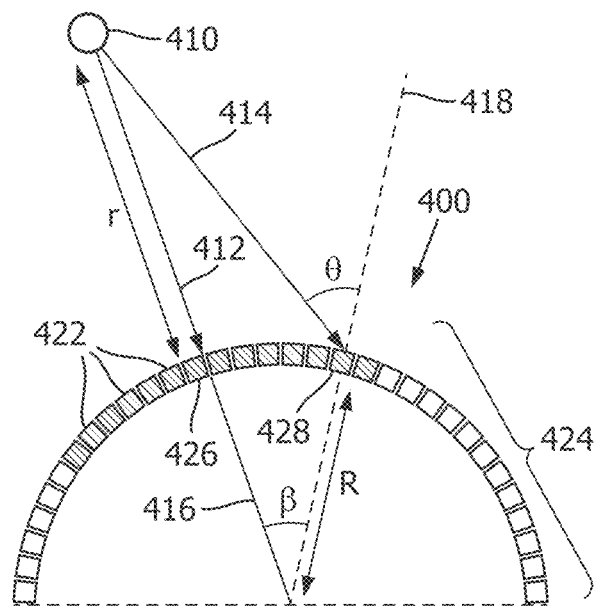
FIG. 7A is a diagrammatic schematic view of an array of acoustic elements receiving reflected ultrasonic energy from an on-axis target object, according to aspects of the present disclosure.
Figure 7B:
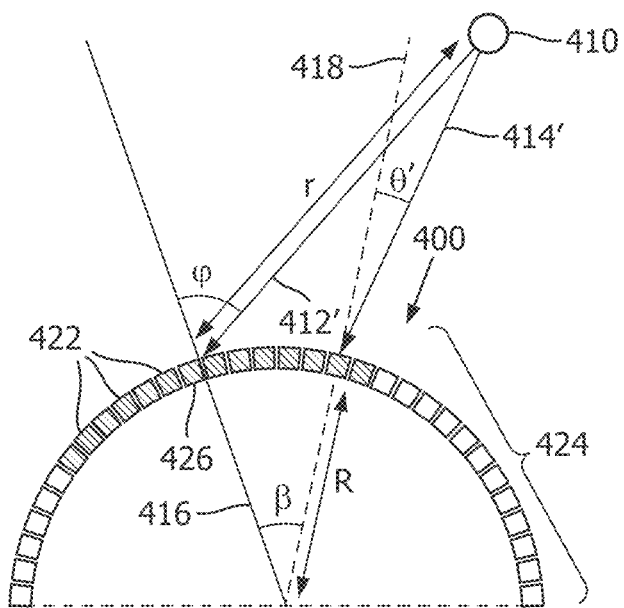
FIG. 7B is a diagrammatic schematic view of an array of acoustic elements receiving reflected ultrasonic energy from an off-axis target object, according to aspects of the present disclosure.

FIGS. 7A and 7B depict a portion of an array 400 of acoustic elements receiving ultrasound signals reflected by a target object 410 at different positions relative to a center axis 416 of an aperture. The array 400 is an IVUS imaging array disposed in a circular pattern with a radius R around a circumference of the imaging assembly. However, any array of acoustic elements is contemplated, such as a linear array, a curvilinear array, arrays for external ultrasound, two-dimensional arrays, 1.X-dimensional arrays, etc. As shown in FIGS. 7A and 7B, a first portion 422 of the acoustic elements of the array are grouped together and activated as an aperture, while other acoustic elements 424, which are not part of the aperture, are not activated. The acoustic elements 422 of the aperture are activated according to a scan sequence to transmit ultrasound energy and receive echoes associated with the transmitted signals. In some embodiments, the scan sequence is performed by activating a single acoustic element at a time to transmit ultrasound energy and/or receive echoes corresponding to the transmitted ultrasound energy. The position or index of each element in the aperture can be described by the angle $\beta$ between the line perpendicular to the center of the active aperture and the line perpendicular to the element.

In FIG. 7A, a target object 410 is shown at a first, on-axis position reflecting ultrasound energy to the elements of the array 400. The first portion 422 of the elements of the array are activated as an aperture, which includes the shaded elements. A second portion 424 of the elements of the array are not activated and not included in the aperture. The aperture includes a first element 426 and a second element 428. The target object 410 reflects a first portion 412 of ultrasonic energy toward the first element 426, and a second portion 414 of ultrasonic energy toward the second element 428. Each element of the array 400 can receive ultrasonic energy from a range of angles of acceptance. The angle of acceptance $\theta$ is the angle between the radial center line 418 of the second element 428 and the direction of the received second portion 414 of ultrasonic energy. In that regard, because the first portion 412 of energy is aligned with the radial center line of the first element 426, and therefore aligned with the center of the aperture (i.e. $\beta=0°$), the angle of acceptance of the first portion 412 of ultrasonic energy by the first element 426 is 0°. By contrast, as the second element 428 is off-center from the aperture (i.e. $\beta \neq 0°$), the angle of acceptance $\theta$ of the second portion 414 of ultrasonic energy on the second element 428 is significantly larger, for example, approximately 55°. However, because the first and second portions 412, 414 of ultrasonic energy are reflected by the target object 410 when it is aligned with the center axis 416 of the aperture, both the first and second portions 412, 414 of ultrasonic energy are considered to be on-axis contributions to the signal received by the aperture.

In FIG. 7B, the target object 410 is shown at a second, off-axis position reflecting ultrasound energy to the elements of the array 400. The target object 410 reflects a first portion 412' of energy to the first element 426, positioned at the center of the aperture 422, and a second portion 414' of energy to the second element 428. Although the angle of acceptance $\theta'$ between the center axis 418 of the second element 428 is closer to 0° than the angle $\theta$ of acceptance shown in FIG. 6A, the angle of arrival $\varphi$, which measured between the center axis 416 of the aperture (i.e. the first element 426) and the first portion of energy 412', is significantly greater than 0°. In other words, the energy reflected by the target object 410 when it is in the second position is off-axis (i.e. $\varphi \neq 0$). By contrast, when the target object 410 is in the first position, energy reflected by the target object toward the aperture is on-axis (i.e. $\varphi=0$).

As mentioned above, side lobe and grating lobe artifacts appear because a portion of ultrasonic energy is reflected from off-axis objects to elements in an aperture. In other words, grating lobe artifacts result when acoustic elements of a spatially-undersampled array receive ultrasonic energy at relatively large angles of acceptance. The present disclosure describes systems and methods for reducing image clutter and artifacts by taking into account the directional receive characteristics of the apertures of the array. In some aspects, embodiments of the present disclosure involve grouping transmit-receive pairs of an aperture into right and left subapertures, and comparing the signals received by each subaperture in order to identify which signals are image clutter and which signals correspond to on-axis scans of tissue.

As also mentioned above, each individual element of an array can receive ultrasound energy from a wide range of acceptance angles. However, the amplitude of a signal generated by an element changes depending on the angle of acceptance. This characteristic of acoustic elements in an array is referred to as directivity. The directivity of the acoustic elements in the array can be described as the directional sensitivity of the acoustic elements to signals received at different angles. The directivity of the elements is manifested in the amplitude response of an aperture, and can be characterized by the mathematical relationship:

$$f(\theta) = \frac{\sin(\pi d/\lambda \sin\theta)}{\pi d/\lambda \sin\theta} \cos\theta$$

where d is the element width, $\lambda$ is the wavelength of the received ultrasonic energy, and $\theta$ is the acceptance angle between the target object (e.g., target object 410) or source of the signal and the element. For a circular array, such as an array of an IVUS imaging catheter, the acceptance angle $\theta$ can be determined using the mathematical relationship:

$$\theta = \beta + \tan^{-1}\left(\frac{R\sin\beta}{R(1-\cos\beta)+r}\right)$$

where R is the radius of curvature of the array, and r is the range or distance between the target object and the center of the active aperture. It will be understood that θ can be determined by other relationships when the array is not circular. It will be further understood that the relationship for directivity shown above may be approximate and based upon certain boundary conditions. In practice, acoustic elements may have a more rapid "fall off" as a function of angle than expressed by the relationship above. For example, Selfridge, et al., "A theory for the radiation patter of a narrow-strip acoustic transducer," Appl. Phys. Lett. 37 (a), Jul. 1, 1980, which is hereby incorporated by reference in its entirety, provides further information and relationships for characterizing the directivity of an array of acoustic elements.

Figure 8:
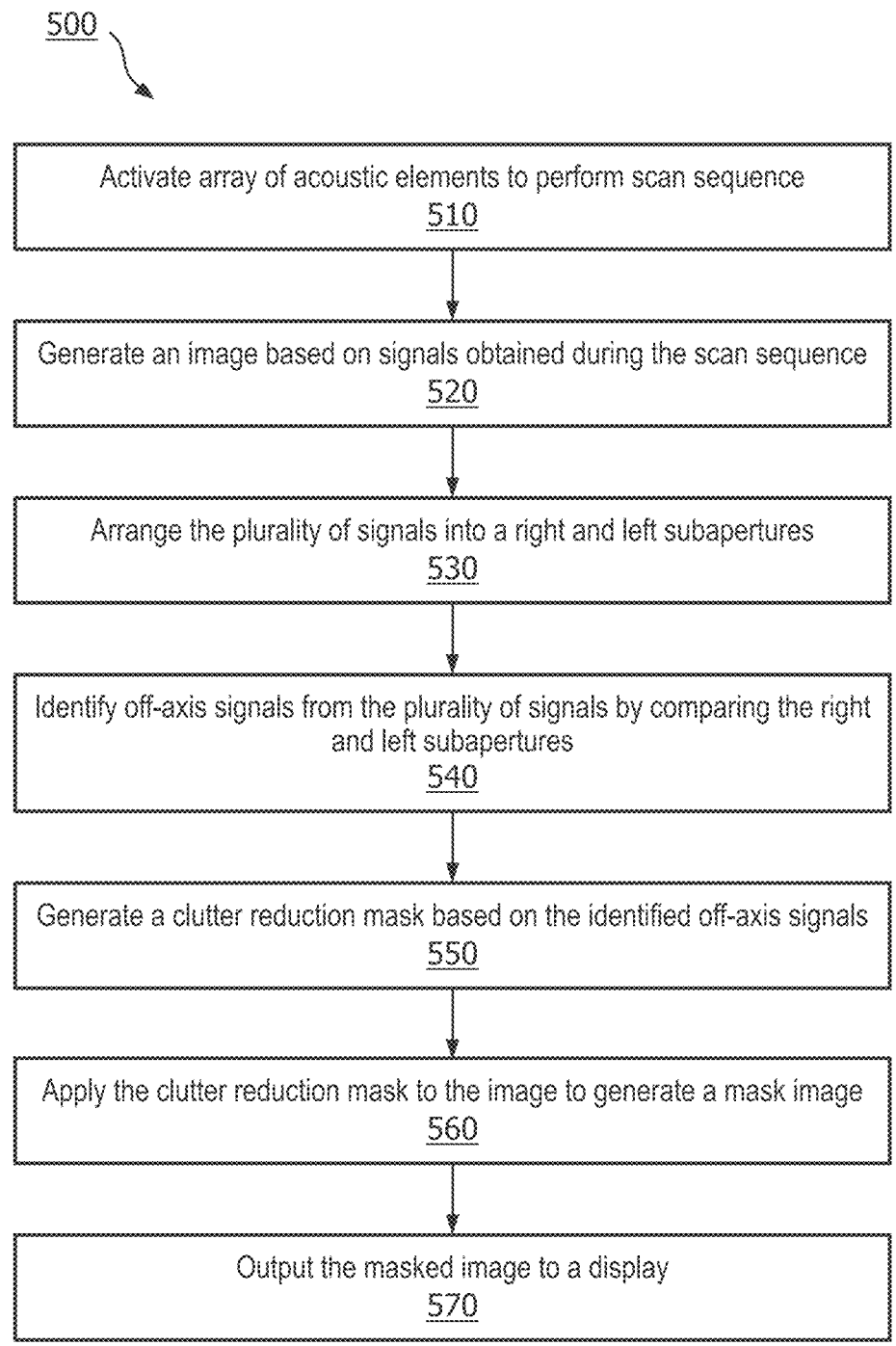
FIG. 8 is a flow diagram illustrating a method for generating a reduced clutter ultrasound image, according to aspects of the present disclosure.

Because grating lobe artifacts are the result of ultrasonic signals reflected by objects that are off-axis from an aperture image clutter can be reduced, minimized, or eliminated by comparing signals or image data received by different spatial groups of transmit-receive pairs of an aperture, even for a spatially-undersampled array. In that regard, FIG. 8 illustrates a method 500 for reducing or minimizing artifacts and image clutter in an ultrasound image.

In step 510, a processor or controller activates an array of acoustic elements to perform a scan sequence, such as the scan sequence 300 shown in FIG. 5. In some embodiments, the array may be an annular array of an IVUS imaging catheter, such as the array 124 shown in FIGS. 6A and 6B. However, other types of arrays may also be used, such as external ultrasound imaging probes, intracardiac echocardiography (ICE) catheters, transesophageal echocardiography (TEE) probes, transthoracic echocardiography (TTE) probes, or any other suitable array-based ultrasound imaging device. Further, while exemplary embodiments of the present disclosure may describe one-dimensional arrays used to generate two-dimensional images, other types of arrays can be used, such as 1.5D arrays, 1.XD arrays, or 2D arrays for generating three-dimensional images.

The scan sequence may be performed by activating apertures of the array to form focused beams of ultrasound energy. In an exemplary embodiment, the scan sequence includes activating a sequence of transmit-receive pairs that scans in a reciprocating pattern around or across the array until every element of the array has been fired. Groups of transmit-receive pairs associated with a respective group of (e.g., fourteen) contiguous acoustic elements are arranged into apertures. In other embodiments (e.g., external ultrasound probe), multiple elements are simultaneously activated to transmit and/or receive ultrasound energy. In step 520, an image is generated based on the signals received by the apertures of the array. In one embodiment, received ultrasound signals corresponding to each transmit-receive pair of an aperture are combined by delay-and-sum beamforming to generate a single line of an image. The image is formed by generating at least one image line (e.g., A-line) for each aperture of the array and arranging the summed image lines into the image.

Figure 9A:
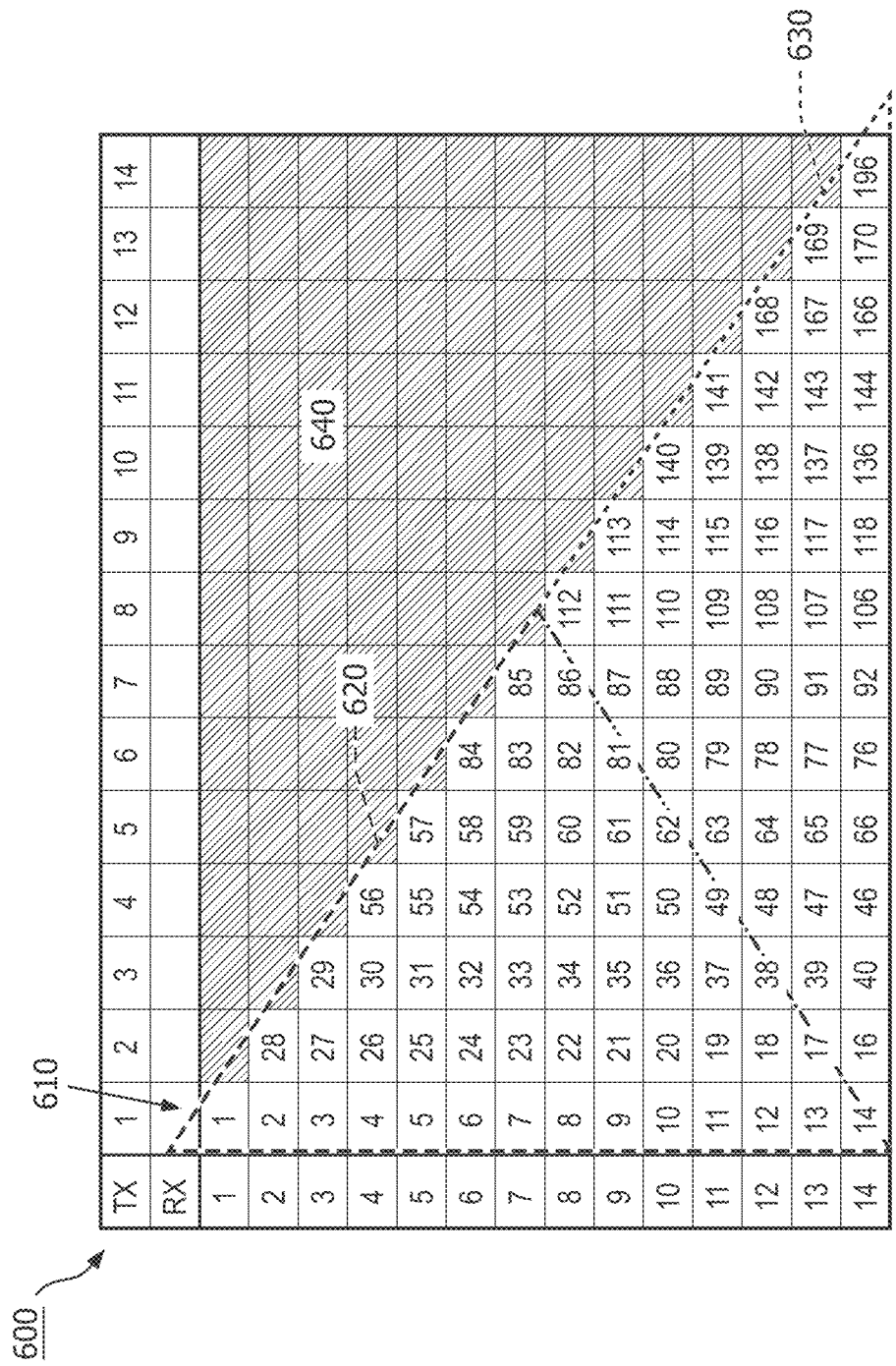
FIG. 9A is a diagrammatic graphical view of an aperture of an ultrasound scan sequence including a right subaperture and a left subaperture, according to aspects of the present disclosure.
Figure 9B:
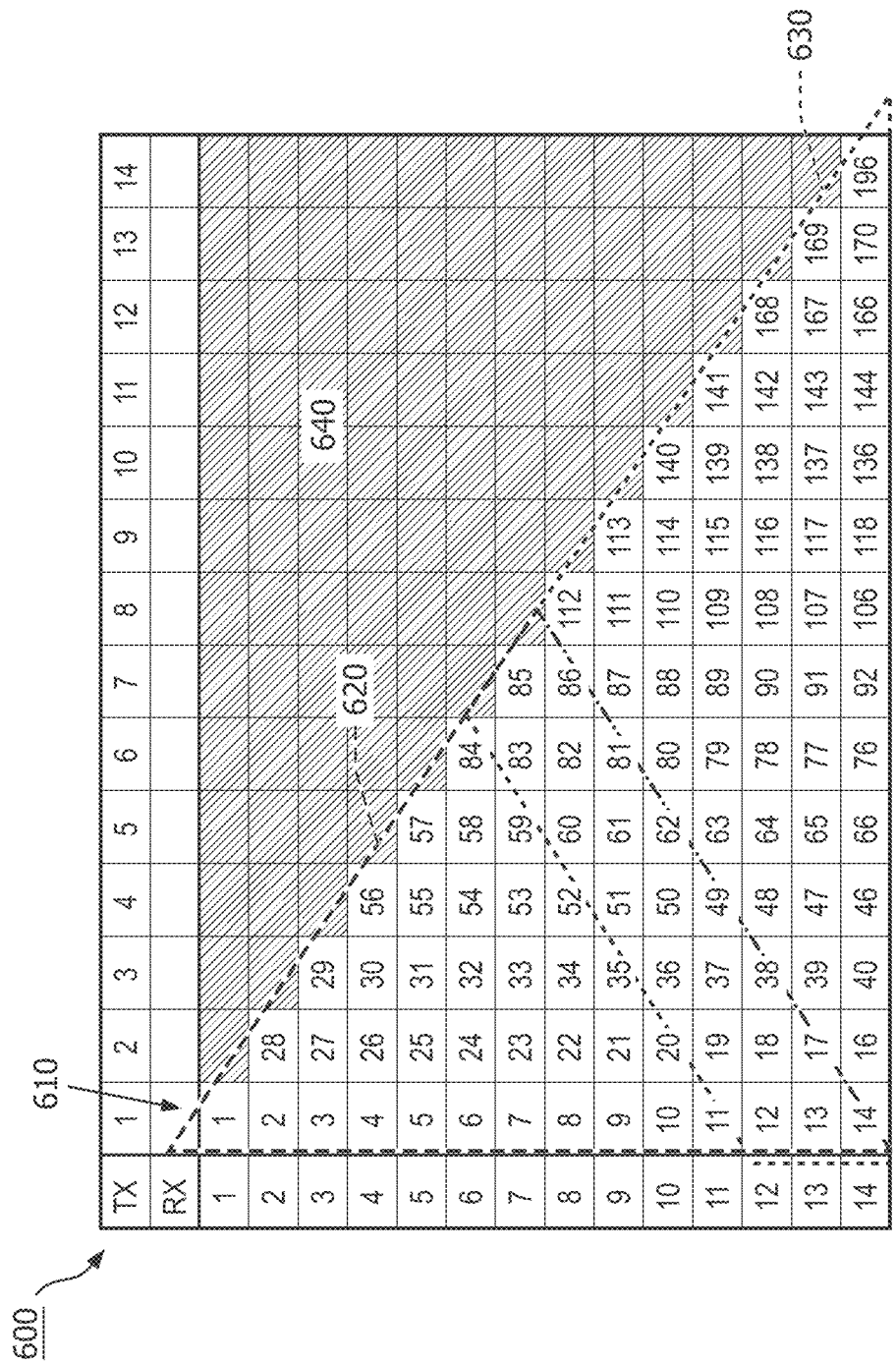
FIG. 9B is a diagrammatic graphical view of an aperture of an ultrasound scan sequence including overlapping right and left subapertures, according to aspects of the present disclosure.

In step 530, the transmit-receive pairs of each aperture obtained by the scan sequence for each aperture are further divided into subapertures. In that regard, FIG. 9A illustrates a portion of a scan sequence 600 in which individual transmit-receive pairs of an aperture 610 are arranged into a right subaperture 620 and left subaperture 630. However, in other embodiments, an aperture can be divided into more than two subapertures, such as a left subaperture, a right subaperture, and a middle subaperture. The divided supaertures may or may not overlap, and may contain different amounts of transmit-receive pairs. FIG. 9B shows a portion of the a scan sequence 600 in which the subapertures overlap. The aperture 610 is represented by a triangular grouping of transmit-receive pairs in which the transmit-receive pairs form a cascading, "zig-zag" pattern around an annular array of acoustic elements. The aperture 610 spans 14 contiguous elements of the array. The region 640 of the sequence 600 represents transmit-receive pairs that are not necessarily activated due to the signal reciprocity rule. In that regard, because signals transmitted by element 1 and received by element 2 should equal signals transmitted by element 2 and received by element 1, it is not necessary to perform both transmit-receive pairs. Where only one of two reciprocal transmit-receive pairs is activated in an aperture and used in the beamforming summation, its weighting in the summation may be suitably adjusted (for instance by doubling) to compensate for the missing contributions from the unactivated transmit-receive pair.

The left subaperture 620 corresponds to a first portion of transmit-receive pairs of the aperture that are transmitted using elements 1 through 7, and received by elements 1 through 14. The right subaperture 630 corresponds to a second portion of transmit-receive pairs of the aperture 610 that are transmitted using elements 1 through 14 and received by elements 7 through 14. In that regard, the left subaperture 620 can be more associated with the left side of the aperture 610 than the right side of the aperture 610, and the right subaperture 630 can be more associated with the right side of the aperture 610 than the left side of the aperture 610. As further explained below with respect to FIG. 10, the association of a given transmit-receive pair to an area of an aperture (e.g., right, left, middle) can be described by an index based on a sum of the transmit and receive indices of the transmit-receive pair, rather than by the sequential or temporal indices used for the transmit-receive pairs in FIGS. 9A and 9B. More generally, we can define a left subaperture as any subaperture with a mean spatial frequency lower than the mean spatial frequency of the full aperture, and a right subaperture as any subaperture with a mean spatial frequency greater than the mean spatial frequency of the full aperture. The inventive technique is applicable to some degree to any left/right subaperture pairs so defined.

In step 540, the signals obtained by the left subaperture 620 and right subaperture 630 are compared to identify which signals are associated with reflections from targets (e.g., tissue structures) that are on-axis with the aperture, and which signals are associated with off-axis reflections and/or noise. The signals of the right and left subapertures can be compared according to a plurality of relationships in order to identify different aspects of an image. In that regard, by comparing the signals from the different subapertures of each aperture, different image layers can be generated or isolated. For example, an image clutter layer can be isolated in order to generate an image clutter mask in order to reduce the presence or influence of artifacts and/or noise in the image. In one embodiment, step 540 includes using a mathematical relationship to generate a clutter reduction mask or image layer. For example, a grating lobe image layer can be generated using the formula:

$$\text{Grating Lobe Estimate} = 1 - \frac{\text{abs}(\text{abs}(\text{Left}) - \text{abs}(\text{Right}))}{\max(\text{abs}(\text{Left}), \text{abs}(\text{Right}))}$$

where abs(Left) is the absolute value of the beamformed signal for the left subaperture and abs(Right) is the absolute value of the beamformed signal for the right subaperture. The above relationship can be performed for all apertures of an array and at each depth to generate a grating lobe reduction mask or layer. Further, a noise image layer can be generated using the formula:

$$\text{Noise Estimate} = 1 - \frac{\sqrt{\text{abs}(\text{abs}(\text{Left}) - \text{abs}(\text{Right})) * \text{abs}(\text{abs}(\text{Left}) + \text{abs}(\text{Right}))}}{\max(\text{abs}(\text{Left}) + \text{abs}(\text{Right}))}$$

When calculating the grating lobe estimate and noise estimate, a smoothing filter can be applied to the abs(Left) and abs(Right) to reduce noise and prevent excess sparseness in the masks. For example, some grating lobe artifacts may be acceptable in the areas of the image representative of tissue rather than lumen, and therefore may not reduced in the tissue region. In step 550, an image clutter reduction mask can be generated using the formula:

Clutter Reduction Estimate=Grating Lobe Estimate*
(1−Noise Estimate)

It will be understood that the relationships above are exemplary and that the grating lobe estimate, noise estimate, and clutter reduction estimate can be generated using different relationships. For example, in one embodiment, the grating lobe estimate relationship could be modified such that the denominator is the mean of (abs(Left), abs(Right)), rather than the maximum. Further, the relationships can be augmented using, for example, flow information and auto-boarding information while using the same kernel ideology.

The clutter reduction estimate is calculated for each scan line and each depth in order to generate the clutter reduction mask. Generating the clutter reduction mask can further include performing smoothing or spatial low-pass filtering on the clutter reduction estimate. For example, a 2D average image kernel, log, threshold and power can be used in smoothing and generating the clutter reduction mask. Time gain control (TGC) curves can also be used to modify the mask so that the clutter reduction can be applied differently among different depths. For example, the clutter reduction mask could be applied more aggressively in the near field (more likely representative of lumen), and less aggressively in the far field (where more noise is likely present). In step 560, the clutter reduction mask is applied to the original beamformed image to reduce or eliminate the presence of image clutter, such as side lobes, grating lobes, and/or noise. The clutter reduction mask can be applied by, for example, a multiplication of the original beamformed image with the clutter reduction mask, or subtracting the clutter reduction mask from the original image in log domain. In order to reduce tissue sparseness, the mask can also be applied to the full beamformed image through a multiplication and then blending the clutter reduced image with the original data. For example, the grating lobe estimate could be generated using the relationship:

Grating Lobe Estimate=min(abs(BM),abs(Right),abs
(Left))

where abs(BM) is the absolute value of the full beamformed image. A blended clutter reduced image or mask can then be generated using the relationship:

Blended GL Reduced Estimate=CRE*BF+(1CRE)
*Grating Lobe Estimate where CRE is the clutter reduction estimate or mask calculated above, and BF is the full beamformed image data. In step 570, the masked image produced in step 560 is output to a user display in communication with the processor.

In some embodiments, the clutter reduction procedures described above can be used in conjunction with Dual Apodization, cross-correlation, Dual Apodization with cross-correlation (DAX), and/or beamspace off-axis postfilter techniques to further improve clutter reduction. Exemplary techniques are described in, for example, Chi Hyung Seo and Jesse T. Yen, "Sidelobe Suppression in Ultrasound Imaging using Dual Apodization with Cross-correlation", IEEE Trans Ultrason Ferroelectr Freq Control. 2008 October 55 (10) 2198-2210; U.S. Pat. No. 8,254,654; International Publication No. PCT/EP2018/074690, filed Sep. 13, 2018; and U.S. Provisional Patent Application No. 62/696,971, filed Jul. 12, 2018, the entireties of which are hereby incorporated by reference.

Figure 10:
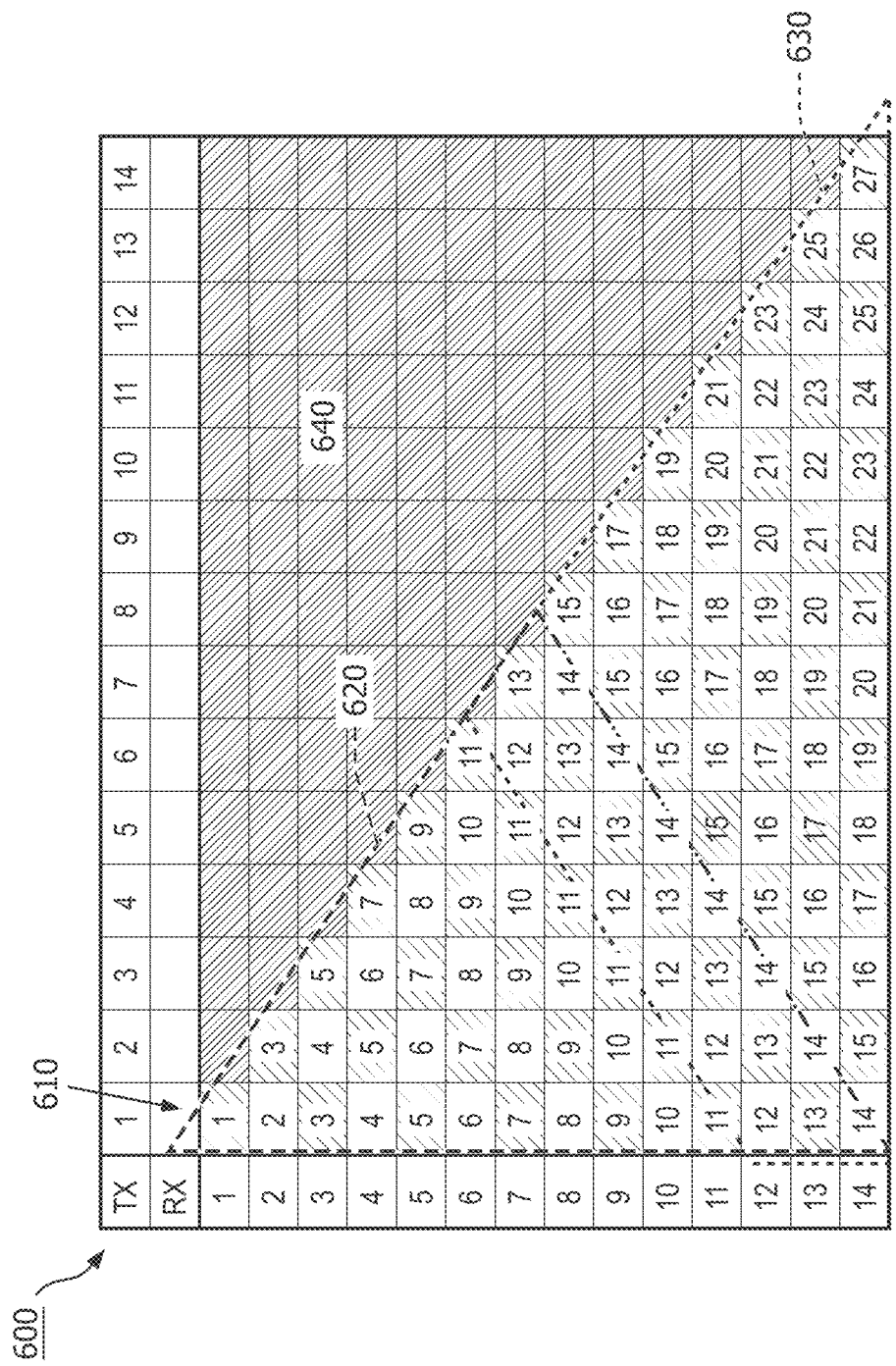
FIG. 10 is a diagrammatic graphical view of an aperture of an ultrasound scan sequence including a right subaperture and a left subaperture that are further divided into even and odd subapertures, according to aspects of the present disclosure.

For example, FIG. 10 illustrates an aperture of a scan sequence 600 in which DAX is used in addition to the approaches described in the present application. The aperture 610 is divided into the left subaperture 620 and the right subaperture 630. Each of the right and left subapertures 620, 630 are further divided into even and odd subapertures, which is illustrated by the checkerboard pattern of interleaving white and shaded transmit-receive pairs. It will be understood that, in contrast to the diagrammatic view of the scan sequence of FIGS. 9A and 9B, in which the numerical indices of the transmit-receive pairs correspond to the sequential order of the transmit-receive pair firings, the indices shown in FIG. 10 represent the spatial frequencies of the transmit-receive pairs. The spatial frequency of each transmit-receive pair is determined by adding the transmit element index and the receive element index, and subtracting the added value by one. Transmit-receive pairs with even spatial frequencies will correspond to an even subaperture, and transmit-receive pairs with odd spatial frequency values will correspond to an odd subaperture. Thus, the transmit-receive pair corresponding to transmit element 5 and receive element 9 has a calculated index of (5+9)−1=13, which corresponds to the left odd subaperture. Generally speaking, two subapertures are said to be interleaved if the numerical range of spatial frequencies in the first subaperture overlaps with the numerical range of spatial frequencies in the second subaperture. The left subaperture 620 includes transmit-receive pairs with spatial frequencies of 1 to 14, while the right subaperture 630 includes transmit-receive pairs with spatial frequencies of 15-27. In other embodiments, the spatial frequencies are determined by adding, for each transmit-receive pair, the transmit element index and the receive element index, without subtracting one. As above, transmit-receive pairs with even spatial frequency values will correspond to an even subaperture and transmit-receive pairs with odd spatial frequency values will correspond to an odd subaperture. However, any suitable approach for separating the right and left subapertures for DAX can be used, such as grouping even and odd sequential transmit-receive indices, as illustrated in FIGS. 9A and 9B.

In one example, DAX is first performed separately on the left and right subapertures before generating the grating lobe and noise estimates. Accordingly, for each aperture, four separate subapertures are beamformed: left odd, left even, right odd, and right even. The left odd and even subapertures can be used to form a DAX-suppressed left subaperture, and the right odd and even subapertures can be used to form a DAX-suppressed right subaperture.

Figure 11:
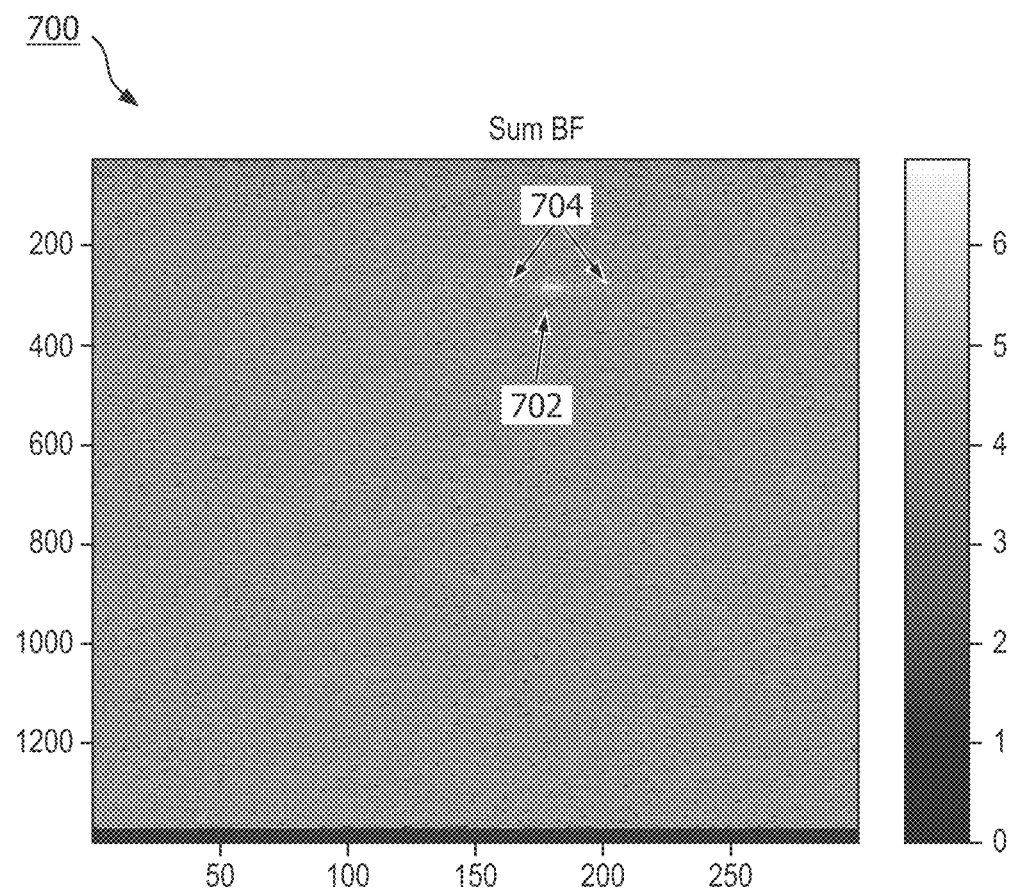
FIG. 11 is a full beamformed ultrasound image, according to aspects of the present disclosure.
Figure 12A:
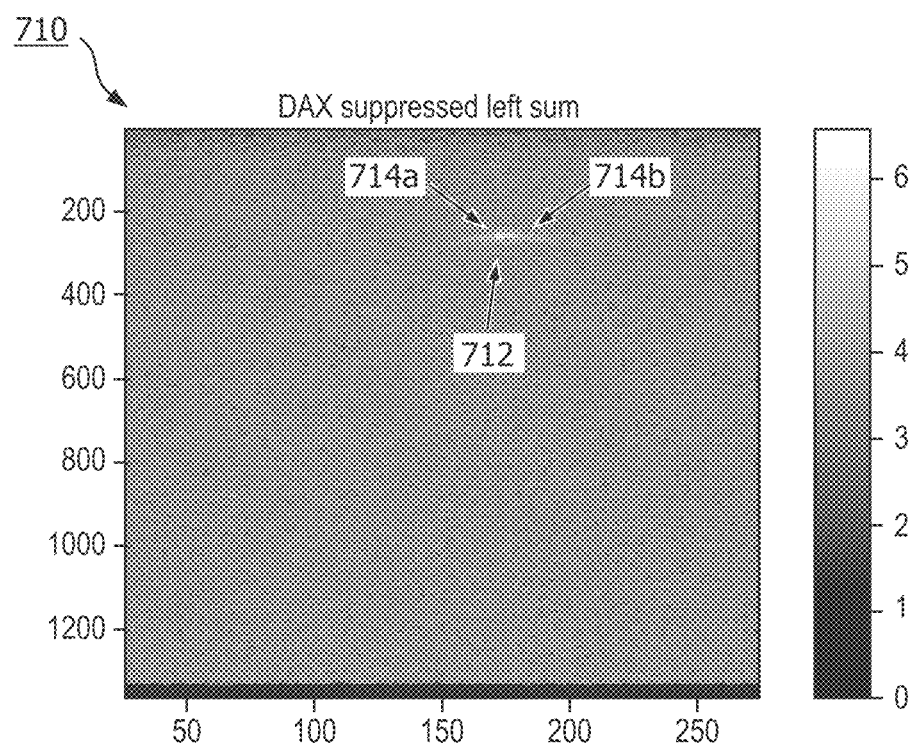
FIG. 12A is a beamformed ultrasound image generated using left subapertures, according to aspects of the present disclosure.
Figure 12B:
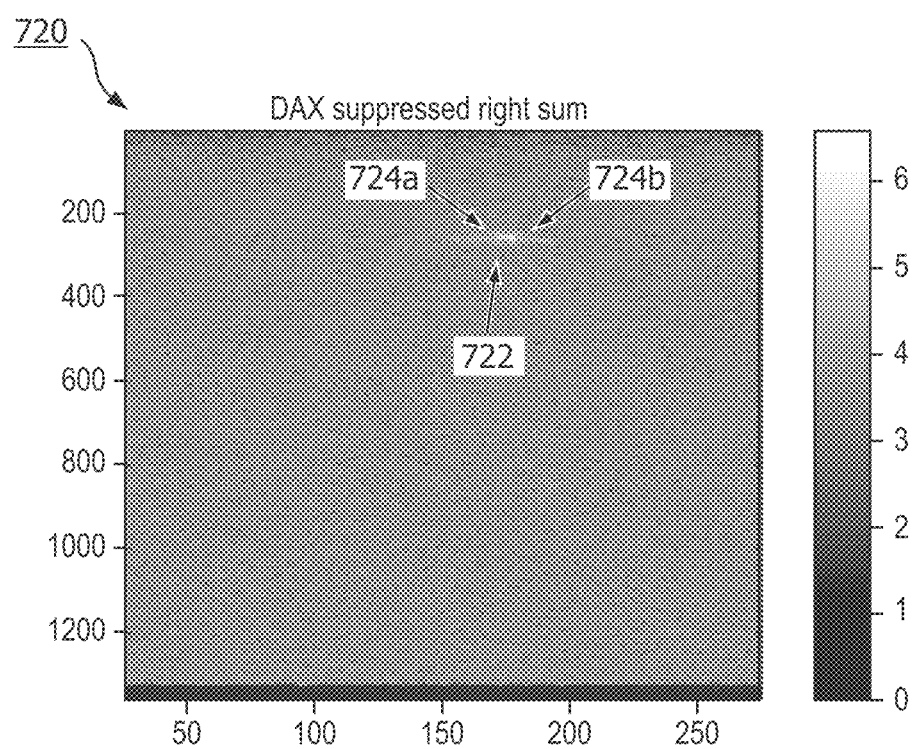
FIG. 12B is a beamformed ultrasound image generated using right subapertures, according to aspects of the present disclosure.

FIGS. 11 and 12A-12D illustrate the processes and results of the method 500 on an ultrasound image of a target. In that regard, FIG. 11 shows an ultrasound image that includes a target 702, which is shown as a bright spot near the top of the image 700. However, the image 700 also shows tails 704, which are artifacts that may be the result of side lobes and/or grating lobes. These artifacts add unwanted clutter to the image, and can complicate diagnostic processes for the physician. FIGS. 12A and 12B show images corresponding to the image 700 shown in FIG. 11, which are generated using left and right subapertures, respectively, where both right and left subapertures are first suppressed using a DAX process. For FIGS. 12A and 12B, a DAX procedure was first applied to each of the right and left subapertures to further reduce side lobe and grating lobe artifacts. In that regard, in FIG. 12A, the image 710 shows a relatively smaller tail 714a on the left side of the target 712, and a relatively larger, longer tail 714b on the right side of the target. Conversely, the image 720 in FIG. 12B shows a relatively larger or longer tail 724a on the left side of the target 722, and a relatively shorter, or smaller tail 724b on the right side of the target 722. Accordingly, FIGS. 12A and 12B illustrate that the presence and location of artifacts in an image will change depending on which spatially-corresponding subapertures are used, while the position and/or presence of true, on-axis targets remains substantially the same.

Figure 12C:
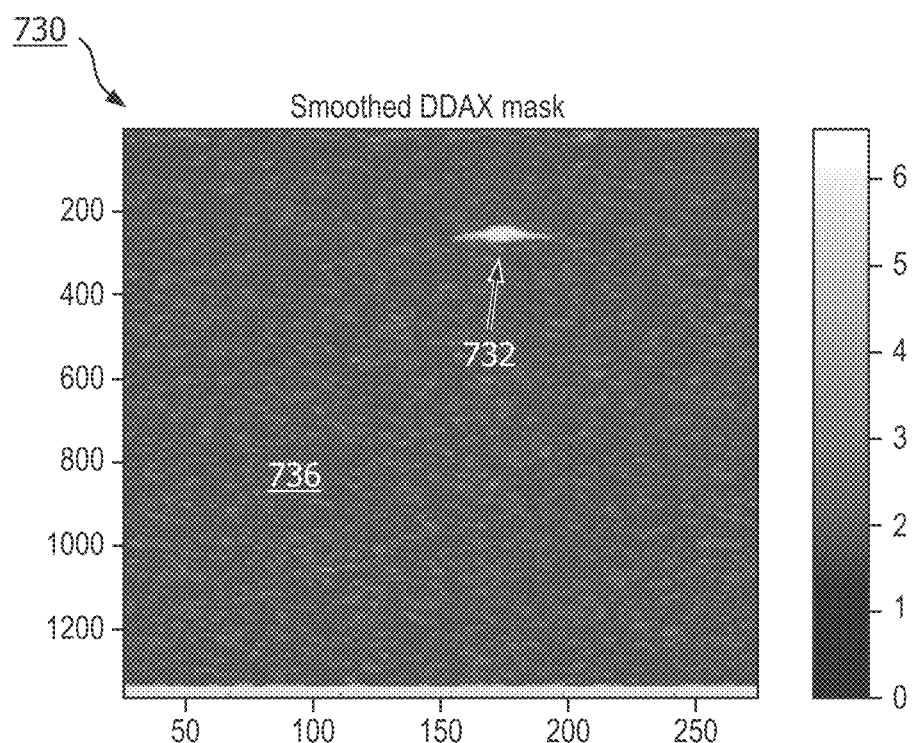
FIG. 12C is an image of a clutter reduction mask, according to aspects of the present disclosure.
Figure 12D:
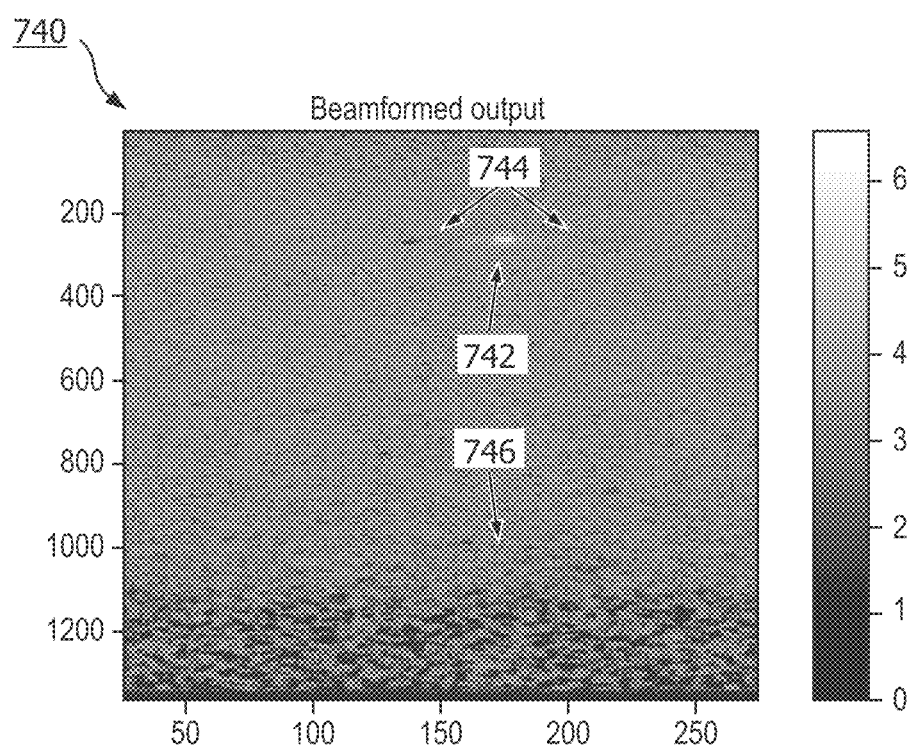
FIG. 12D is an image of a masked image with reduced clutter, according to aspects of the present disclosure.

FIG. 12C shows a clutter reduction mask 730 which is generated based on a comparison of the right and left subapertures, as described with respect to step 540 of the method 500. As shown, the bright spot 732 of the mask 730 shows which parts of the image 700 likely correspond to an on-axis target, while the dark area 736 shows which parts of the image are not likely to be representative of on-axis targets. Because the only true reflector in the image 700 shown in FIG. 11 is the target 702, there is only a single bright spot 732 in the mask 730 of FIG. 12C. FIG. 12D shows a masked image, or clutter reduced image 740 generated by applying the clutter reduction mask shown in FIG. 12C to the original beamformed image shown in FIG. 11. A target 742 is shown in the same location as in FIG. 11. However, the presence or influence of the tail artifacts 744 are significantly reduced. It will be understood that, due to the point spread functions (psfs) of the aperture and subapertures used to generate the image 700 and the mask 730, the tails 744 of the target 742 may not be completely eliminated in some instances. Furthermore, the masked image 740 shows a darkened area 746, which corresponds to greater depths or ranges from the array. In that regard, signals shown at these depths are more likely attributed to noise, and less likely to be representative of tissue. Accordingly, the darkened area includes a greater amount of pixels of low intensity compared to the original beamformed image 700 shown in FIG. 11.

Figure 13A:
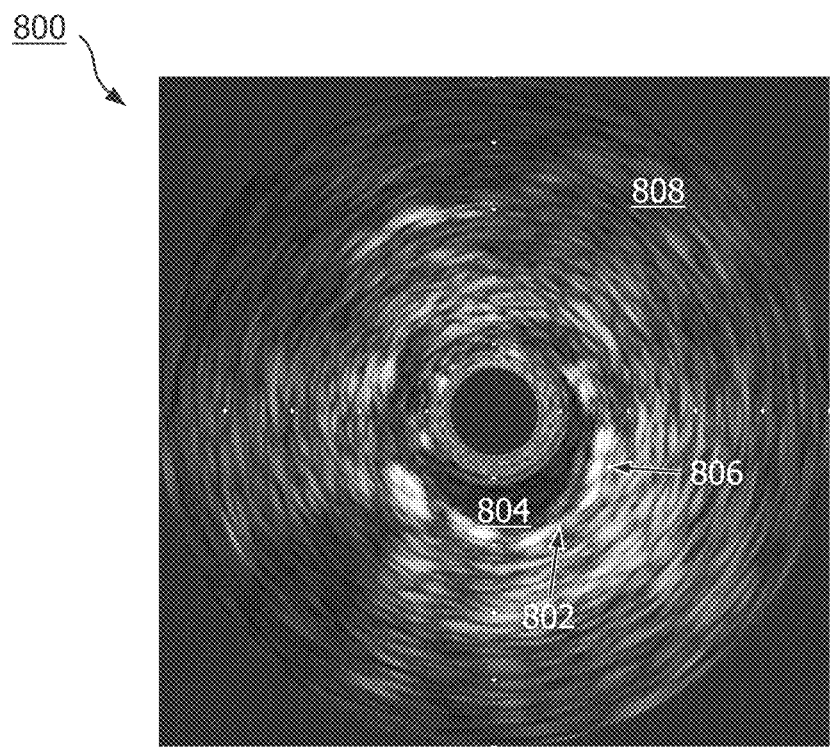
FIG. 13A is a full beamformed IVUS image, according to aspects of the present disclosure.
Figure 13B:
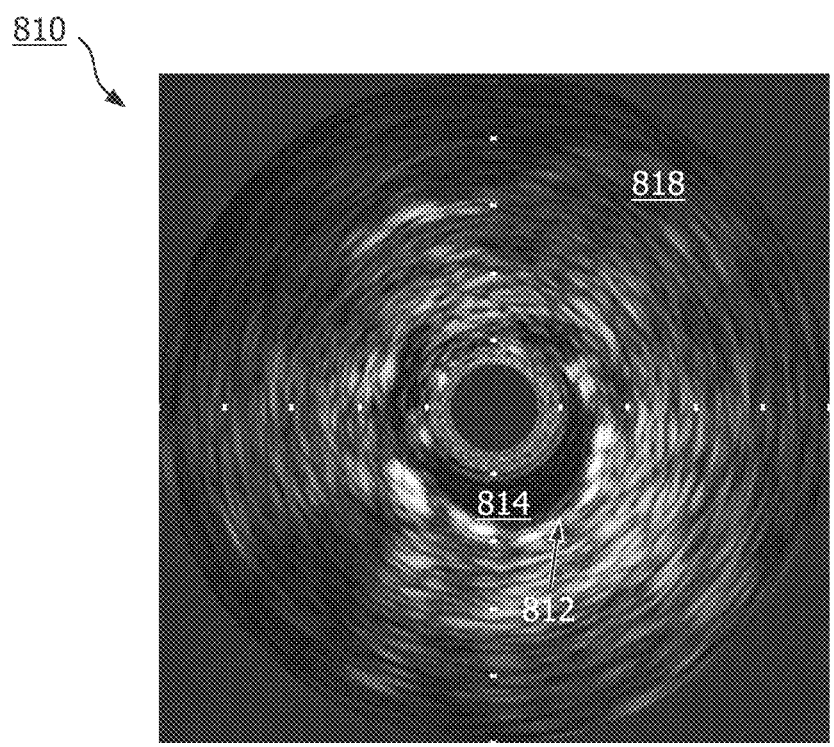
FIG. 13B is a clutter reduced IVUS image, according to aspects of the present disclosure.

FIGS. 13A and 13B show an original beamformed IVUS image 800, and a clutter-reduced image 810 generated using the procedures described above. In that regard, the FIG. 13A includes image clutter 802 within a lumen area 804 of the image 800. The clutter 802 may be caused by side lobes and/or grating lobes from strong reflectors, such as stent struts 806. The image 800 also includes a tissue area 808, which may be referred to as tissue "speckle," and represents reflections from tissue outside the vessel lumen 804. As mentioned above, it may be desirable to reduce or eliminate the clutter 802, without adversely affecting the appearance of the tissue are 808. FIG. 13B shows a clutter-reduced image 810 generated by applying the techniques described above to the image 800 of FIG. 13A. The image includes an area 812 in the lumen region 814 that corresponds to the image clutter 802 shown in FIG. 13A. The area 812 has significantly reduced image artifacts compared to the original image 800. However, the tissue region 818 remains substantially intact, with the tissue speckle still visible. Accordingly, a physician may more readily identify image features (e.g., lumen border, stent struts, tissue) in the clutter-reduced image 810 compared to the original beamformed image 800.

Figure 14A:
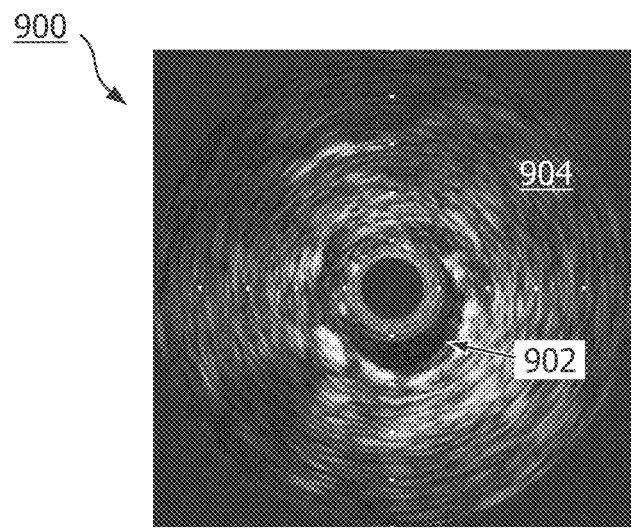
FIG. 14A is a full beamformed IVUS image, according to aspects of the present disclosure.
Figure 14B:
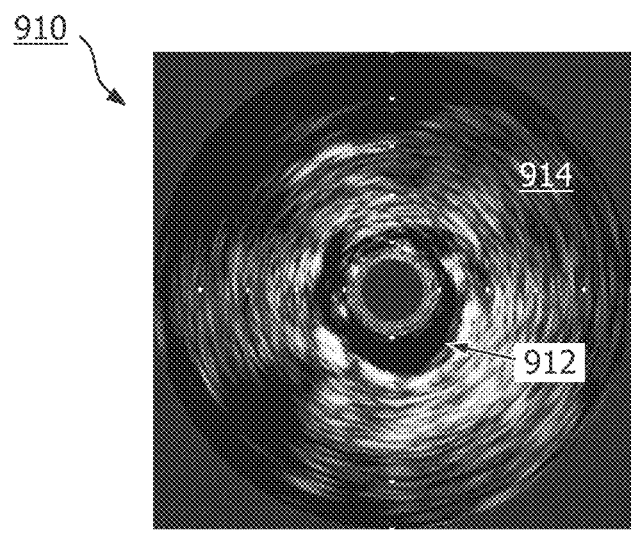
FIG. 14B is a tissue image layer of an IVUS image, according to aspects of the present disclosure.
Figure 14C:
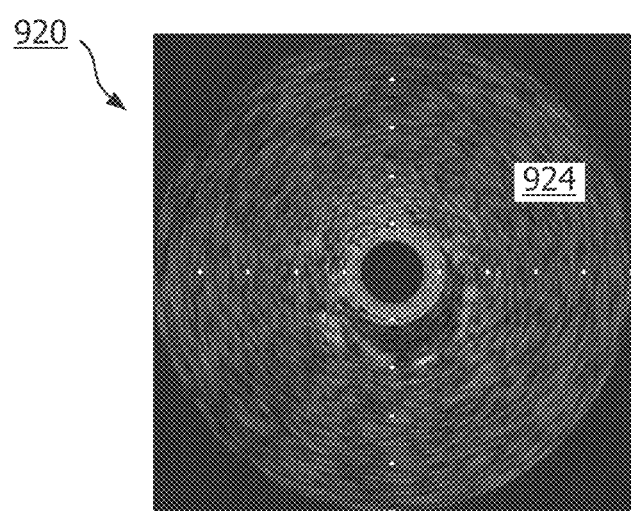
FIG. 14C is a noise image layer of an IVUS image, according to aspects of the present disclosure.

In some aspects, the techniques described above can be used to generate or isolate layers of a beamformed image that are representative of different features that make up the original beamformed image, such as tissue reflections, noise, and clutter. In that regard, FIGS. 14A-14C illustrate a full beamformed image 900, a tissue image layer 910, and a noise image layer 920, respectively. The tissue image layer 910 and the noise image layer 920 are generated from the data used to form the original, full beamformed image 900. For example, the tissue image layer 910 isolates only those signals generated from on-axis signals, and are thus more likely to be representative of tissue rather than image artifacts or noise. Accordingly, the tissue image layer 910 includes a clutter area 912 that exhibits reduced clutter when compared to the clutter area 902 of the image 900. The remaining tissue region 914 may be similar, but not necessarily identical to the corresponding tissue region 904 shown in FIG. 14A. In that regard, the tissue region 914 of the tissue image layer 910 may exhibit more dark areas when compared to the tissue area 904 of the original image 900, due to the clutter and noise reduction in the tissue region of the image layer 910. FIG. 14C is a noise image layer 920 that isolates the components of the original image 900 that correspond to, or likely correspond to noise in the image. In that regard, although the noise 924 shown in the noise image layer 920 is not representative of on-axis reflections from tissue, it may be aesthetically desirable to include some or all of the noise 924 in a clutter-reduced image. Accordingly, in some embodiments, a clutter reduced image that is output to a user display may maintain some amount of noise, particularly in the regions of the image that correspond to tissue.

In one embodiment, the tissue image layer 910 can be isolated or generated by applying the Clutter Reduction Estimate to the full beamformed image, and applying a time-gain control (TGC) and gain to isolate the tissue components of the image. The noise image layer 920 can similarly be generated by applying the clutter reduction estimate to the full beamformed image, and applying a TGC and gain as appropriate to isolate the noise components of the image. Frame averaging and other image parameters can also be used in generating the tissue and noise image layers. The resulting image can be normalized based on the noise and tissue gains used to generate the noise and tissue image layers.

Figure 15A:
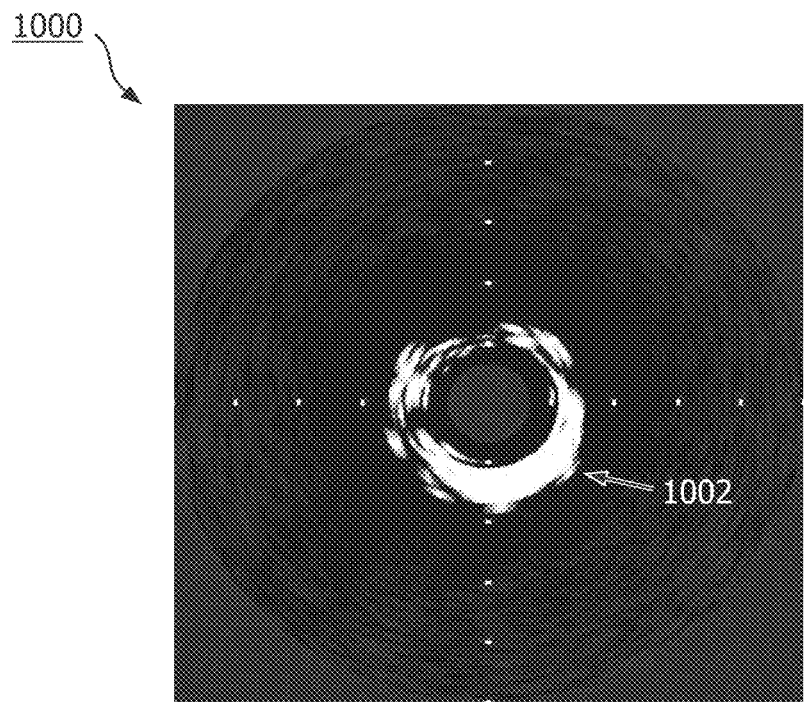
FIG. 15A is a lumen image layer of an IVUS image, according to aspects of the present disclosure.
Figure 15B:
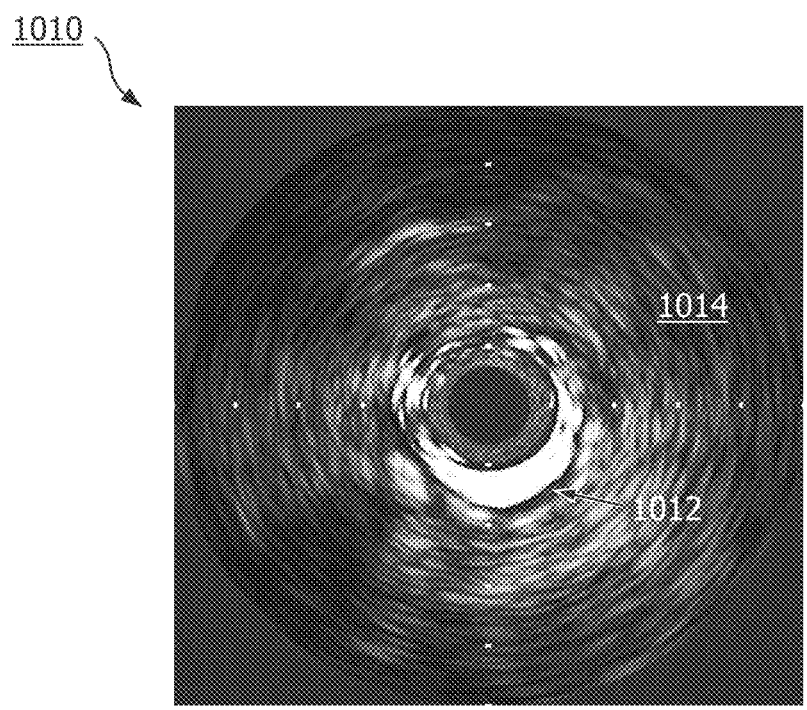
FIG. 15B is a lumen-augmented IVUS image, according to aspects of the present disclosure.

The techniques described above can also be used to isolate image components corresponding to a vessel lumen. For example, the techniques described above can be used to generate a lumen image layer. In that regard, FIGS. 15A and 15B illustrate a lumen image layer 1000 and a lumen-augmented IVUS image 1010, respectively. The lumen image layer 1000 shows a lumen region 1002, and excludes other image features corresponding to tissue or image clutter. The lumen image layer 1000 can be used by a physician to more easily identify the area of an image corresponding to a vessel lumen. The lumen layer can be generated using the formula:

Lumen Estimate=abs(Grating Lobe Estimate)*(1−Clutter Reduction Estimate)

Similar with the tissue and noise image layers, 2D average image kernel, log, threshold, and TGC can be used to smooth and generate the lumen mask or image layer 1000. Ringdown masking and flow masking can also be used in generating the lumen mask 1000. For example, flow image data obtained using blood flow imaging techniques can be combined with the lumen image layer 1000 in order to more accurately distinguish between a lumen, and tissue, which can include echo-lucent plaque. FIG. 15B shows a lumen-augmented IVUS image 1010 in which the lumen image layer 1000 is combined with a full IVUS image to identify a lumen region 1012, and distinguish the lumen region 1012 from a tissue region 1014.

It will be understood that one or more of the steps of the method 500, such as controlling the array to transmit and receive ultrasound energy, generating the image, arranging the signals into right and left subapertures, generating the clutter reduction mask, and outputting the masked image to the display, can be performed by one or more components of an ultrasound imaging system, such as the processor, a multiplexer, a beamformer, a signal processing unit, an image processing unit, or any other suitable component of the system. For example, activating a scan sequence may be carried out by a processor in communication with a multiplexer configured to select or activate one or more elements of an ultrasound transducer array. In some embodiments, generating the ultrasound images may include beamforming incoming signals from the ultrasound imaging device and processing the beamformed signals by an image processor. The processing components of the system can be integrated within the ultrasound imaging device, contained within an external console, or may be a separate component.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ultrasound imaging system, comprising:
an array of acoustic elements configured to transmit acoustic energy into an anatomy and receive echoes corresponding to the transmitted acoustic energy; and
a processor in communication with the array and configured to:
activate the array to perform a scan sequence to obtain a plurality of signals;
generate an image based on the plurality of signals;
arrange the plurality of signals into a first right subaperture, a second right subaperture, a first left subaperture, and a second left subaperture;
use the first right subaperture with a first apodization function and the second right subaperture with a second apodization function to generate a dual apodization with cross-correlation (DAX)-suppressed right subaperture;
use the first left subaperture with a third apodization function and the second left subaperture with a fourth apodization function to generate a dual apodization with cross-correlation (DAX)-suppressed left subaperture;
identify off-axis signals from the plurality of signals by comparing the DAX-suppressed right subaperture and the DAX-suppressed left subaperture;
generate a clutter reduction mask based on the identified off-axis signals;
apply the clutter reduction mask to the image to generate a masked image; and
output the masked image to a display in communication with the processor.

2. The ultrasound imaging system of claim 1,
wherein the scan sequence comprises a plurality of transmit-receive pairs associated with the acoustic elements of the array,
wherein the plurality of signals corresponds to the plurality of transmit-receive pairs,
wherein the first right subaperture comprises a first portion of the transmit-receive pairs and the second right subaperture comprises a second portion of the transmit-receive pairs, wherein the first portion of the transmit-receive pairs and the second portion of the transmit-receive pairs are interleaving,
wherein the first left subaperture comprises a third portion of the transmit-receive pairs and the second left subaperture comprises a fourth portion of the transmit-receive pairs, wherein the third portion of the transmit-receive pairs and the fourth portion of the transmit-receive pairs are interleaving.

3. The ultrasound imaging system of claim 1, wherein the processor is configured to generate a noise image layer based on a relationship that includes the DAX-suppressed right subaperture and the DAX-suppressed left subapertures, wherein the noise image layer comprises an image layer formed of signals representative of noise in the image.

4. The ultrasound imaging system of claim 3, wherein the processor is configured to generate the clutter reduction mask based in part on the noise image layer.

5. The ultrasound imaging system of claim 1, wherein the processor is configured to generate a tissue image layer based on a relationship that includes the DAX-suppressed right subaperture and the DAX-suppressed left subapertures, the image, and the clutter reduction mask, wherein the tissue image layer comprises an image layer formed of signals representative of tissue in the image.

6. The ultrasound imaging system of claim 5, wherein the processor is configured to generate a lumen image layer based on the tissue image layer and the clutter reduction mask, wherein the lumen image layer comprises an image layer formed of signals representative of a body lumen in the image.

7. The ultrasound imaging system of claim 1, where the first and second left subapertures and the first and second right subapertures are part of an aperture, and wherein the aperature comprises an axis.

8. The ultrasound imaging system of claim 7, wherein the first and second left subapertures is spatially associated with the left side of the axis of the aperture and the first and second right subapertures is spatially associated with the right side of the axis of the aperture.

9. The ultrasound imaging system of claim 7, wherein the aperture is associated with an angular portion of a circumference of the array.

10. The ultrasound imaging system of claim 7, wherein the off-axis signals are generated from ultrasound energy reflected from objects that are away from the axis of the aperture.

11. The ultrasound imaging system of claim 7,
wherein the aperture is formed of a plurality of transmit-receive pairs of the scan sequence,
wherein each of the plurality of transmit-receive pairs is associated with a transmit element of the aperture and a receive element of the aperture,
wherein the right subaperture is formed of a first portion of the plurality of transmit-receive pairs representative of all of the transmit elements of the aperture and a portion of the receive elements of the aperture, and
wherein the left subaperture is formed of a second portion of the plurality of transmit-receive pairs representative of a portion of the transmit elements of the aperture and all of the receive elements of the aperture.

12. The ultrasound imaging system of claim 1, further comprising an intravascular ultrasound (IVUS) imaging catheter, and wherein the array of acoustic elements is positioned around a perimeter of the IVUS imaging catheter.

13. A method for ultrasound imaging, comprising:
activating an array of acoustic elements to perform a scan sequence to obtain a plurality of signals;
generating, by a processor in communication with the array, an image based on the plurality of signals;
arranging, by the processor, the plurality of signals into a first right subaperture, a second right subaperture, a first left subaperture, and a second left subaperture;
using the first right subaperture with a first apodization function and the second right subaperture with a second apodization function to generate a dual apodization with cross-correlation (DAX)-suppressed right subaperture;
using the first left subaperture with a third apodization function and the second left subaperture with a fourth apodization function to generate a dual apodization with cross-correlation (DAX)-suppressed left subaperture;
identifying, by the processor, off-axis signals from the plurality of signals by comparing the DAX-suppressed right subaperture and the DAX-suppressed left subaperture;
generating, by the processor, a clutter reduction mask based on the identified off-axis signals;
applying, by the processor, the clutter reduction mask to the image to generate a masked image; and
outputting the masked image to a display in communication with the processor.

14. The method of claim 13,
wherein activating the array to perform the scan sequence comprises activating a plurality of transmit-receive pairs associated with the acoustic elements of the array,
wherein the plurality of signals corresponds to the plurality of transmit-receive pairs,
wherein the first right subaperture comprises a first portion of the transmit-receive pairs and the second right subaperture comprises a second portion of the transmit-receive pairs, wherein the first portion of the transmit-receive pairs and the second portion of the transmit-receive pairs are interleaving,
wherein the first left subaperture comprises a third portion of the transmit-receive pairs and a second left subaperture comprises a fourth portion of the transmit-receive pairs, wherein the third portion of the transmit-receive pairs and the fourth portion of the transmit-receive pairs are interleaving.

15. The method of claim 13, further comprising generating a noise image layer based on a relationship that includes the DAX-suppressed right subaperture and the DAX-suppressed left subaperatures, wherein the noise image layer comprises an image layer formed of signals representative of noise in the image.

16. The method of claim 15, further comprising generating the clutter reduction mask based on the noise image layer.

17. The method of claim 13, further comprising generating a tissue image layer based on a relationship that includes the DAX-suppressed right subaperture and the DAX-suppressed left subaperatures, the image, and the clutter reduction mask, wherein the tissue image layer comprises an image layer formed of signals representative of tissue in the image.

18. The method of claim 17, further comprising generating a lumen image layer based on the tissue image layer and the clutter reduction mask, wherein the lumen image layer comprises an image layer formed of signals representative of a body lumen in the image.

19. The ultrasound imaging system of claim 12,
wherein the IVUS imaging catheter is configured to be positioned within a blood vessel,
wherein the anatomy comprises the blood vessel such that the anatomy is positioned outside of the array of acoustic elements.

* * * * *